(12) United States Patent
Skelton et al.

(10) Patent No.: US 8,280,517 B2
(45) Date of Patent: Oct. 2, 2012

(54) AUTOMATIC VALIDATION TECHNIQUES FOR VALIDATING OPERATION OF MEDICAL DEVICES

(75) Inventors: Dennis M. Skelton, Bloomington, MN (US); Emmanuel R. Darne, Woodbury, MN (US); Justin Kemp, St. Louis Park, MN (US); Nicholas S. Mairs, Minneapolis, MN (US); Brian Sorenson, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 477 days.

(21) Appl. No.: 12/548,227

(22) Filed: Aug. 26, 2009

(65) Prior Publication Data

US 2010/0076525 A1 Mar. 25, 2010

Related U.S. Application Data

(60) Provisional application No. 61/098,384, filed on Sep. 19, 2008.

(51) Int. Cl.
*A61N 1/18* (2006.01)
(52) U.S. Cl. .......................................................... 607/48
(58) Field of Classification Search ................... 607/19, 607/48, 63
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |
| 4,543,955 A | 10/1985 | Schroeppel | |
| 4,550,736 A | 11/1985 | Broughton et al. | |
| 4,566,456 A | 1/1986 | Koning et al. | |
| 4,771,780 A | 9/1988 | Sholder | |
| 4,776,345 A | 10/1988 | Cohen et al. | |
| 4,846,180 A | 7/1989 | Buffet | |
| 4,846,195 A | 7/1989 | Alt | |
| 5,031,618 A | 7/1991 | Mullett | |
| 5,040,534 A | 8/1991 | Mann et al. | |
| 5,040,536 A | 8/1991 | Riff | |
| 5,058,584 A | 10/1991 | Bourgeois | |
| 5,125,412 A | 6/1992 | Thornton | |

(Continued)

FOREIGN PATENT DOCUMENTS

DE 19831109 1/2000

(Continued)

OTHER PUBLICATIONS

Partial International Search Report dated Nov. 5, 2009.

(Continued)

*Primary Examiner* — Brian T Gedeon
(74) *Attorney, Agent, or Firm* — Beth L. McMahon

(57) ABSTRACT

Techniques for validating operation of a medical device are disclosed. A data collection phase utilizes a first sensor carried by a patient to record patient parameter values indicative of conditions experienced by the patient (e.g., posture states.) Therapy parameter values describing therapy adjustments requested by the patient in response to the conditions are also recorded. Associations formed between the therapy parameter values and the patient parameter values are used to develop a closed-loop algorithm for control of an IMD having a sensor similar to the first sensor. An automated device such as a robotic arm uses the recorded patient parameter values to automatically reproduce, and to subject the IMD to, conditions present during the data collection phase. Therapy delivered by the IMD while under control of the closed-loop algorithm and while being subjected to the conditions is compared to the recorded therapy parameter values e to validate IMD operation.

35 Claims, 13 Drawing Sheets

U.S. PATENT DOCUMENTS

| | | |
|---|---|---|
| 5,154,180 A | 10/1992 | Blanchet et al. |
| 5,158,078 A | 10/1992 | Bennett et al. |
| 5,167,229 A | 12/1992 | Peckham |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen et al. |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |

| Patent/Publication | Date | Inventor |
|---|---|---|
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile et al. |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget |
| 2007/1050026 | 6/2007 | Bourget |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison |
| 2008/0114219 A1 | 5/2008 | Zhang |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |

| | | |
|---|---|---|
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| DE | 10024103 | 11/2001 |
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | WO97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

PCT International Search Report dated Jan. 22, 2010.
"Analysis of heart rate dynamics by methods derived from non-linear mathematics: Clinical applicability and prognostic significance," http://herkules.oulu.fi.isbn9514250133/html, 4 pp., 2004.
"Design Competition: Runners-Up for the Best Three Designs," EPN, vol. 26, No. 1, 1 pg., 2002.
"IBM and Citizen Watch develop Linux-Based WatchPad," http://wwwlinuxdevices.com/news/NS6580187845.html, 5 pp., 2006.
"MiniMitter® Physiological and Behavioral Monitoring for Humans and Animals," http://www.minimitter.com/Products/Actiwatch, 3 pp., 2006.
"Watch," Wikipedia, 6 pp., http://en.wikipedia.org/wiki/Watch, 2006.
Aminian et al., "Physical Activity Monitoring Based on Accelerometry: Validation and Comparison with Video Observation," Medical & Biological Engineering and Computing, vol. 37, No. 2, pp. 304-308, 1999.
Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.
Ang et al., "Physical model of a MEMS accelerometer for low-g motion tracking applications," 2004 IEEE International Conference on Robotics and Automation, vol. 2, pp. 1345-51, 2004.
Buchser et al., "Improved Physical Activity in Patients Treated for Chronic Pain by Spinal Cord Stimulation," Neuromodulation, vol. 8, Issue 1, pp. 40-48, Mar. 2005.
Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.

Husak, "Model of Tilt Sensor Systems," ICECS 2002, 9th IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp, May 1994.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp. 2008.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp., Mar. 2007.

Tuisku, "Motor Activity Measured by Actometry in Neuropsychiatric Disorders," Department of Psychiatry, University of Helsinki, Helsinki, Finland, 115 pp., 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99—9th Int'l Traide Fair and Conference for Sensors/Transducers & Systems, Nürnberg, Germany, May 18-20, 1999, Sensor '99 Proceedings II, A 5.2, pp. 47-52, 1999.

U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

| Record | Activity Level | Posture | Amplitude (V) | Pulse Width (µs) | Frequency (Hz) | Electrode Configuration | Adjustment |
|---|---|---|---|---|---|---|---|
| 1 | A1 | [X1, Y1, Z1] | 2.0 | 150 | 10 | 1+ 2- | +.2V |
| 2 | A2 | [X2, Y2, Z2] | 2.5 | 200 | 50 | 1- 2+ | -.1V |
| 3 | A3 | [X3, Y3, Z3] | 1.0 | 100 | 40 | 3- 2+ | -.5V |
| 4 | A4 | [X4, Y4, Z4] | 6.6 | 100 | 40 | 1- 3+ | 0 |
| 5 | A5 | [X5, Y5, Z5] | 8.3 | 100 | 35 | 8- 6+ | +.3V |

AUTOMATIC VALIDATION TECHNIQUES FOR VALIDATING OPERATION OF MEDICAL DEVICES

RELATED APPLICATIONS

The following application claims priority to provisionally-filed U.S. patent application entitled "Automatic Validation Techniques for Validating Operation of Medical Devices", Patent Application Ser. No. 61/098,384 filed Sep. 19, 2008, which is incorporated herein by reference in its entirety.

TECHNICAL FIELD

The disclosure relates to medical devices and, more particularly, to automatic validation of medical devices that deliver therapy.

BACKGROUND

A variety of types of medical devices are used for chronic, e.g., long-term, provision of therapy to patients. As examples, pulse generators are used for chronic provision of cardiac pacing and neurostimulation therapies, and pumps are used for chronic delivery of therapeutic agents, such as drugs. Typically, such devices provide therapy continuously or periodically according to parameters, e.g., a program comprising respective values for each of a plurality of parameters, specified by a clinician.

In some cases, the patient is allowed to activate and/or modify the therapy. For example, the symptoms, e.g., the intensity of pain, of patients who receive spinal cord stimulation (SCS) therapy may vary over time based on the activity level or posture of the patient, the specific activity undertaken by the patient, or the like. For this reason, a patient who receives SCS therapy from an implantable medical device (IMD), e.g., an implantable pulse generator, is often given a patient programming device that communicates with his IMD via device telemetry, and allows the patient to activate the neurostimulation and/or adjust the intensity of the delivered neurostimulation.

It is advantageous to associate patient therapy adjustments with one or more measurable parameters. After this association is made, a device may automatically deliver therapy to the patient according to those adjustments whenever the one or more parameters are detected. U.S. patent application Ser. No. 11/607,454 entitled "Closed-Loop Therapy Adjustment" filed Dec. 1, 2006, assigned to the assignee of the current disclosure, and which is incorporated by reference herein in its entirely, describes techniques for detecting a value of a sensed patient parameter, and automatically delivering therapy to a patient according to recorded therapy adjustment information previously associated with the detected value. According to these techniques, a therapy adjustment is received from the patient or other user and, in response to the adjustment, a sensed value of a patient parameter is stored with the therapy information determined based on the adjustment. The association may be made automatically or after user confirmation. Therapy may then be delivered according to the associated therapy information whenever the parameter value is subsequently detected. In this manner, as an example, a medical device that delivers therapy to the patient may "learn" to automatically adjust the therapy in the manner desired by the patient as the sensed parameter of the patient changes.

SUMMARY

Techniques for validating operation of a medical device are disclosed. The techniques may be used to validate operation of a medical device that delivers therapy in a closed-loop manner in response to patient parameter values that are sensed by a sensor. In examples described below, the medical device is an implantable medical device (IMD), although this need not be the case, and the disclosed techniques may be used to validate other types of medical devices. Additionally, while examples involving medical devices that deliver electrical stimulation to treat a pain condition are described in detail, other devices that deliver other types of therapy may usefully employ these mechanisms.

According to one example embodiment, the techniques may include a data collection phase and a validation phase. During the data collection phase, the patient is outfitted with an external sensor. For instance, the sensor may be carried on a belt or otherwise affixed to an exterior surface of the patient or to the patient's clothing. In one embodiment, this external sensor is a three-axis accelerometer that detects a patient's posture state comprising at least one of posture and activity state (e.g., activity level, direction of activity, etc.). The data from this sensor is recorded in the form of patient parameter values. Patient parameter values may describe, or are indicative, of a posture state of the patient. The posture state involves at least one of posture and activity level of the patient. The recorded patient parameter values may be associated with timestamps.

During this data collection phase, the IMD may be delivering therapy to the patient. The patient uses a patient programmer to make adjustments to the therapy as needed. A description of the resulting therapy, including therapy changes occurring because of patient adjustments, may be recorded. This description may be recorded by the patient programmer or another recording device, for example. The recorded therapy description may be described as therapy parameter values (e.g., stimulation amplitude, stimulation pulse width, electrode configuration, etc.). This description may include timestamps.

After the therapy description and the patient parameter values are recorded, the two sets of data may be correlated to one another. This correlation may be performed using the timestamps, for instance. The correlated data sets may be used to create a test data file that describes a sequence of patient parameter values (e.g., a description of the sequence of posture states assumed by the patient, as detected by a three-axis accelerometer) and a description of the corresponding therapy that was being delivered to the patient while the patient parameter values were recorded. The test data file may be employed to automatically recreate the conditions experienced by the patient during the data collection process. In particular, the patient parameter values from the test file may be provided to an automated device to control operation of an automated device, which may be a robotic arm.

While the automated device is controlled by the patient parameter values from the test file, an IMD affixed to the automated device may be delivering therapy to the patient. This IMD may be configured to execute a closed-loop control algorithm that adjusts the therapy in accordance with a sensor that is contained within, or otherwise accessible to, the IMD. As the automated device re-enacts the posture states, the closed-loop algorithm controlling the IMD will automatically deliver therapy in response to the posture states. The therapy parameter values associated with the delivered therapy may be measured and compared to those recorded during data collection. A miscompare may indicate that a potential problem exists with the IMD design. Therefore, a miscompare will be recorded along with data that may be used by technicians and logic designers to analyze the miscompare situation.

Various methods and techniques for performing automated testing and regression analysis are disclosed herein. These techniques provide a mechanism to very accurately and automatically reproduce a sequence of conditions to which a medical device may be subjected during therapy delivery. Without this ability, validating that a medical device is performing as expected, as may be needed after design changes are made, must be performed by manually re-creating the sequence of conditions. For instance, a patient may be required to manually re-enact a series of activities and postures that were previously performed over a series of days. Such re-creation is not only very tedious, but is also error prone. Moreover, conducting this type of re-enactment is expensive.

One embodiment of the disclosure relates to a method of testing a medical device. The method includes recording therapy parameter values describing therapy being delivered to a patient, and recording a sequence of patient parameter values indicative of at least one of posture and activity of the patient occurring while the therapy is being delivered. The method further includes automatically reproducing the sequence of patient parameter values and validating that the medical device is delivering therapy in accordance with the recorded therapy parameter values. In one example, automatically re-producing the sequence of patient parameter values includes attaching the medical device to an automated device, providing the recorded sequence of patient parameter values to control the automated device, and re-producing, by the automated device, conditions that resulted in sensing the sequence of patient parameter values. The conditions may result in at least one of orienting the medical device in one or more predetermined positions and exposing the medical device to one or more predetermined activity states. The activity states are characterized by at least one of activity level, velocity of activity, acceleration of activity, a direction of velocity or acceleration, or at least one other parameter that describes the activity.

According to another aspect, validating that the medical device is delivering therapy in accordance with the recorded therapy parameters may comprise delivering, by the medical device, therapy in response to a closed-loop algorithm. Recording therapy parameter values may comprise operating a second medical device in response to an open-loop algorithm.

Another embodiment provides a system for automatically testing a medical device. The system includes a therapy delivery module to deliver therapy to a patient according to therapy parameter values, and a sensor to sense patient parameter values indicative of one or more posture states assumed by the patient while the therapy is being delivered. The system also includes an automated system coupled to receive the patient parameter values and the therapy parameter value, to reproduce a sequence of conditions indicated by the patient parameter values, and to validate that the medical device provides therapy according to the therapy parameter values while the medical device is subjected to the reproduced conditions.

Yet another embodiment involves a system to automatically verify operation of an implantable medical device. The system includes a first implantable medical device carried by a patient to deliver therapy to the patient according to therapy parameter values, and a sensor carried by the patient to sense posture states assumed by the patient during delivery of the therapy. This system further comprises an automated device to automatically re-create the posture states and an automated programmer to automatically generate at least some of the therapy parameter values. A second implantable medical device provides therapy in response to the automatically-generated therapy parameter values while being subjected to the automatically re-created the posture states. Compare logic is communicatively coupled to the second implantable medical device to determine whether the therapy provided by the second implantable medical device is substantially similar to the therapy delivered by the first implantable medical device.

The details of one or more embodiments are set forth in the accompanying drawings and the description below. Other features, objects, and advantages of the disclosure will be apparent from the description and drawings, and from the claims.

BRIEF DESCRIPTION OF THE DRAWINGS

FIG. 7 is a chart illustrating an example patient parameter values table that may be used for closed-loop adjustment of therapy.

DETAILED DESCRIPTION

Figure 1:
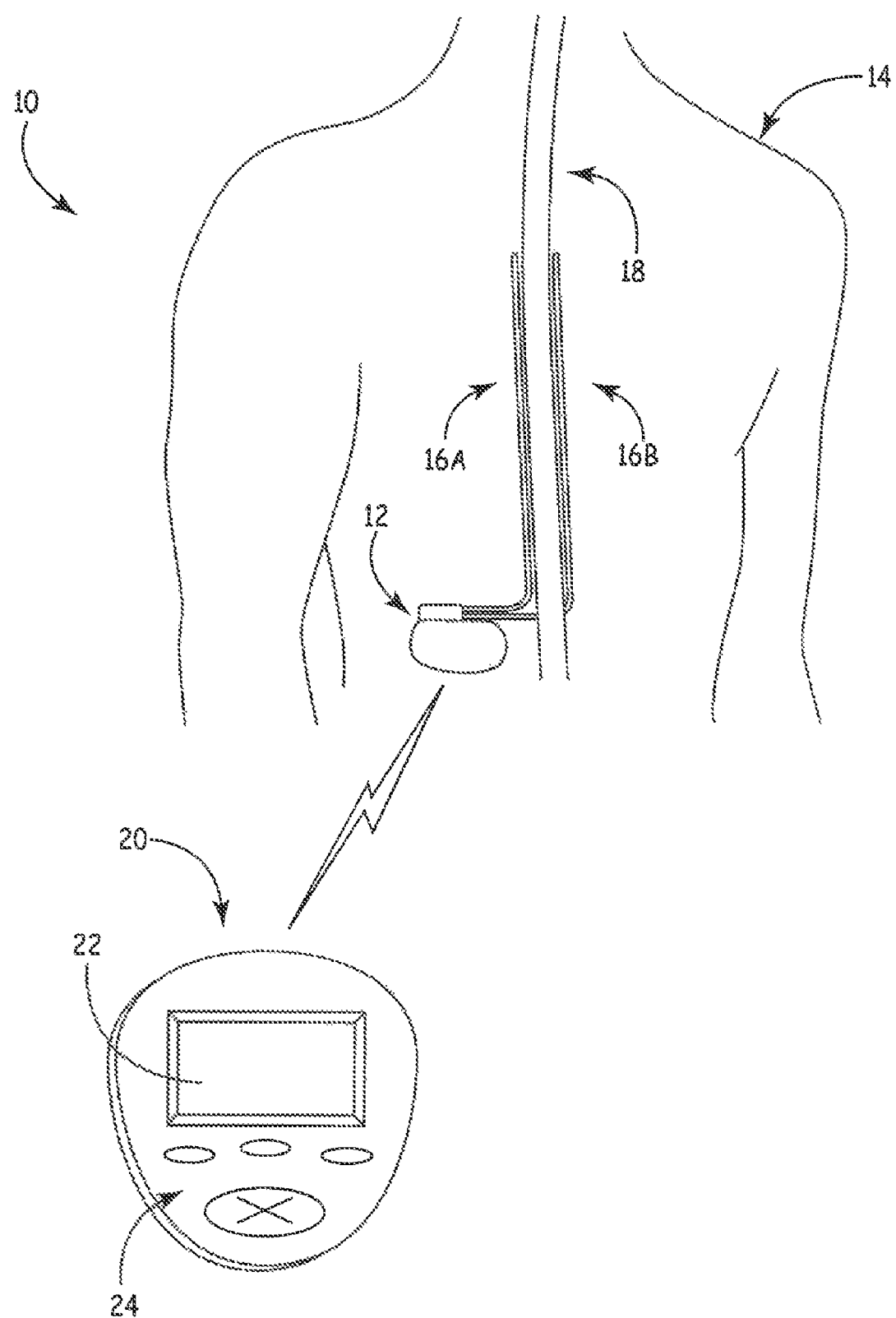
FIG. 1 is a conceptual diagram illustrating an example system that facilitates closed-loop therapy adjustment.

Electrical stimulation is one example of a therapy that may be delivered in a closed-loop manner. Electrical stimulation may be, for example, used to treat patients that suffer from chronic back pain, leg pain, or other pain that cannot be treated through other methods. As a patient changes posture, the stimulation may need to be adjusted in order to maintain efficacy. The patient may use a programmer to manually change one or more stimulation parameters, e.g., amplitude, to adjust the therapy in response to the posture change. Alternatively, the patient may select a new stimulation program that includes new respective values for each of the stimulation parameters to adjust the therapy.

While manual adjustment of stimulation may be effective, the patient is burdened by the need to adjust the therapy throughout a daily routine. Thus, an implantable medical device (IMD) may include, or be coupled to, one or more sensors that sense a patient parameter. The IMD may deliver closed-loop therapy based on values of the patient parameter. The IMD "learns" to provide this closed-loop therapy based on therapy adjustments made by the patient. In particular, during a "learning phase", the IMD associates patient parameter values with therapy information (e.g., therapy adjustments) received from the patient. Later, the IMD may use these associations to automatically deliver therapy. As the IMD senses patient parameter values, the IMD may automatically deliver therapy according to therapy parameters that have been previously associated with the sensed patient parameter values. The patient may rarely need to manually enter an adjustment to the therapy after a medical device learns to automatically adjust the therapy based on sensed patient parameter values.

For example, the IMD may store a table or other data structure that contains records, where each record contains therapy information associated with a respective value of a patient parameter. The IMD may automatically update the table in response to a therapy adjustment from the patient, or may update the table after receiving confirmation that the adjusted therapy is desired. The IMD may update the program table after every adjustment input from the patient, after a complete therapy adjustment that includes a number of inputs, or periodically during therapy.

During design and test of the IMD, and as changes are made to the design of the IMD, it is necessary to validate that the IMD is indeed delivering the appropriate level of therapies as determined by a closed-loop algorithm. To do this, it is helpful to subject the IMD to sequence of conditions that is known to have previously resulted in generation of therapy by the IMD in a predetermined manner. When the IMD is re-exposed to a same sequence of conditions, the resulting therapy generation may then be compared to the expected therapy to determine whether the IMD design is currently responding as expected.

One way to subject the IMD to a sequence of conditions is to use manual intervention. For instance, a patient may be required to re-enact a sequence of activities and postures that were previously enacted and that were known to result in therapy delivery in an expected manner. During this re-enactment, therapy delivery by the IMD may be compared to the expected therapy delivery to detect differences. A change in the way the IMD is reacting to a sequence of conditions may indicate that a design change has unexpectedly altered the way the IMD is responding.

Several problems exist with requiring the type of manual re-enactment of conditions in the manner described above. First, in the scenario wherein the conditions involve posture states, re-enactment generally requires that the patient re-perform each posture and/or activity that was undertaken during the learning phase. This may be time-consuming and tedious for the patient. Moreover, it will likely be difficult for a patient to precisely re-enact each movement in the way it was originally performed. This may result in differences in posture and/or activity level which may, in turn, alter the therapy that is automatically delivered by the IMD. Additionally, ensuring that the patient is accurately re-enacting each posture state using the same timing as previously used is difficult. Such a re-enactment is time-consuming and expensive to conduct.

In accordance with the foregoing challenges, the current disclosure provides techniques for automatically re-enacting a sequence of conditions. This type of re-enactment may be useful for regression testing after design changes are made. This type of re-enactment is also useful when implementing new functionality, as when a new closed-loop algorithm is being incorporated into an IMD. In this case, it may be useful to implement that algorithm in stages such that at first, the algorithm is implemented using an external programmer, such as a patient programmer, and an external sensor. Later, after the algorithm is verified, the algorithm can be incorporated into the IMD. At that point, it is necessary to perform testing to ensure that the IMD is performing as expected using the algorithm. Techniques for addressing these, and other, types of test and design validation scenarios are disclosed.

According to one embodiment, the automated system for re-enacting patient conditions is an automated device such as robotic arm that subjects the device to positions and levels of movement in a manner consistent with a sequence of posture states recorded during a previous learning, or data collection, phase. In particular, according to this embodiment, the automated device is capable of positioning the device in any position within three-dimensional space. This positioning capability thereby mimics any posture that a patient may assume. The automated device is further capable of generating movement while the device is in a given position. This movement may be generated according to an activity parameter that may be associated with acceleration, velocity or an activity level, for instance. This is discussed further below.

As previously mentioned, the current techniques may comprise two phases: a data collection phase and a validation phase. During the data collection phase, the patient is outfitted with an external sensor. For instance, the sensor may be carried on a belt or otherwise affixed to an exterior surface of the patient or to the patient's clothing. In one embodiment, this external sensor is a three-axis accelerometer that detects a patient's posture and an activity parameter (e.g., activity level). The data from this sensor is recorded in the form of patient parameter values. For purposes of the disclosure, patient parameter values describe, or are indicative, of a posture state of the patient. The posture state involves at least one of posture and activity level of the patient. The recorded patient parameter values may be associated with timestamps.

While the external sensor is recording patient parameter values in the foregoing manner, the IMD delivers therapy to a patient. The patient may control this therapy by using a patient programmer. For instance, as the patient transitions from a sitting position to a standing posture, or from a stationary state to an active state, the patient may experience a heightened level of pain. As such, the patient may use the patient programmer to incrementally increase the amplitude of electrical stimulation that is being delivered by the IMD. Such a change may be requested by the patient in anticipation of the posture state transition, during that transition, or sometime after the transition is completed. In a similar manner, the patient may desire to decrease therapy levels, as may occur if a patient transitions from an upright state to a reclining posture.

As the patient uses the patient programmer to modify parameters that control therapy, a description of the delivered therapy is recorded. The therapy description may be expressed in terms of therapy parameter values, which are those parameters that control and adjust delivery of therapy. For electrical stimulation therapy, therapy parameter values may include, for example, current or voltage stimulation amplitude, pulse width, pulse shape, pulse frequency, duty cycles, electrode polarities and configurations, a description of field strength, a description of the programs used to control therapy, and any other parameter or descriptor that describes and/or controls how therapy is being delivered. For other therapies, other types of parameters may be included in this description. For instance, a rate of flow or a bolus of a substance may be recorded for a therapy involving delivery of a substance to a patient.

The description of the delivered therapy may be recorded by the patient programmer or another device associated with this programmer. The recorded therapy description may be recorded in any type of format. For instance, delta values may be recorded that indicate changes reflected by therapy adjustments (e.g., a requested increase in stimulation by 0.2V). By recording an initial therapy level and one or more such delta values, the sequence of therapy adjustments may be reconstructed. Similarly, the recorded description may describe therapy adjustments in terms of normalized values (e.g., a 10% decrease in amplitude, etc.). Alternatively or additionally, absolute values may be recorded, such as resulting stimulation levels (e.g., 5.0 V). Any one or more of these, or other types, of descriptions may be recorded to describe the delivered therapy. The recorded data may include timestamps.

In one embodiment, recording of a therapy description may optionally also be performed by the IMD itself. For instance, the IMD may have a measurement module that determines the manner in which therapy is being delivered to a patient. A description of this measured therapy may be stored within the IMD. If the system is operating properly, any description recorded by the IMD should correspond with the data that is being recorded by the patient programmer or an associated device.

If the medical device includes a sensor, the IMD may further record sensor data. If the IMD sensor is of a same type as the external sensor worn by the patient, the sensor data recorded by the medical device may be compared to the data collected by the external sensor. This comparison may be used to determine whether both sensors are operating properly.

Manual data collection may also be performed during the data collection phase if desired. For instance, the patient may be asked to manually record patient parameter values associated with conditions the patient is experiencing. In the current example, the patient parameter values may indicate posture state changes (e.g., transitioning from lying to standing, or from stationary to active). Such parameter values may be recorded in an eDiary, which may be a personal data assistance (PDA), palm pilot, some other type of handheld electronic device, a laptop computer, an audio and/or video recording device, or some other device to record this information. Such data may include one or more timestamps, for instance. The patient may further be asked to use the eDiary to record any therapy adjustments requested by patient via the use of patient programmer.

Data collection will continue in the foregoing manner for a predetermined period of time (e.g., three days) for a particular patient. Thereafter, some of the various types of data that were collected during this period are correlated to one another to create a test data file. For example, the patient parameter values sensed by the external sensor (e.g., posture and/or activity level) may be correlated with a description of the therapy that was being delivered to the patient at substantially the same time. The correlations between patient parameter values and the therapy parameter values may be created using the stored timestamps. Alternatively, in an embodiment wherein data is collected at regular known time intervals (e.g., every three seconds), the order in which the records are created may be used to make the correlations between the patient parameter values and the therapy parameter values.

After the patient parameter values are associated with therapy parameter values in the above-described manner, the resulting test data file describes a sequence of patient parameter values (e.g., a description of the sequence of posture states assumed by the patient, as detected by a three-axis accelerometer) and the corresponding therapy that was being delivered to the patient while the patient parameter values were recorded. The recorded therapy parameter values will describe any changes in therapy that occurred over time in response to patient-specified therapy adjustments.

If desired, the eDiary entries entered by the patient may be used to validate patient parameter values recorded from the external sensor. For instance, posture states recorded in the eDiary in conjunction with time stamps are used to validate accuracy of the posture states indicated by the patient parameter values sensed by the external sensor. A further validation may compare patient parameter values sensed by any internal sensor of the medical device with those sensed by the external sensor. This additional validation step may be used to verify proper operation of any internal sensor included within the IMD, assuming proper operation of the external sensor has already been confirmed.

Next, a validation phase may be entered wherein the test data file may be used to automatically recreate the conditions experienced by the patient during the data collection phase. In particular, the patient parameter values from the test file may be provided to an automated device, either directly as raw data or in the form of processed data, such as via test scripts. In either case, the patient parameter values are used to control operation of an automated device, which may be a robotic arm.

As an example of the foregoing, the raw data may include a series of accelerometer readings that each comprises at least one of a vector in three-dimensional space and an activity level. This raw data may be provided to a robotic arm to cause the robotic arm to transition through a series of motions corresponding to the postures and activity states (e.g., activity levels) assumed by the patient during data collection. This re-creation of the posture states experienced by the patient during data collection may occur in real-time. That is, the re-creation may occur over the same time period and at the same speed as the posture state transitions were performed by the patient during data collection.

During this validation phase, an IMD that is similar to that which delivered therapy to the patient during data collection is affixed to the automated device in a predetermined manner. Unlike the IMD used during data collection, however, the IMD used during validation will execute a closed-loop control algorithm that adjusts therapy in accordance with a sensor that is contained within, or otherwise accessible to, the IMD. As the automated device re-enacts the posture states in the manner described above, the closed-loop algorithm controlling the IMD will automatically deliver therapy in response to the posture states. The therapy parameter values associated with the delivered therapy may be measured and compared to those recorded during data collection. A miscompare may indicate that a potential problem exists with the IMD design. Therefore, a miscompare will be recorded along with data that may be used by technicians and logic designers to analyze the miscompare situation.

According to another aspect of the disclosure, at least some of the time when a miscompare results, control scripts may be used to prompt an automated programmer to issue a therapy adjustment command to the IMD. This should, in turn, prompt the IMD to adjust therapy according to the levels recorded during the data collection phase. This therapy adjustment may be verified by measuring the resulting therapy parameter values and comparing them against those that were obtained during the data collection phase. This validates the ability of the IMD to respond to changes in the closed-loop operation.

In one embodiment, during data validation, the IMD is pre-loaded with a table or other data structure that stores the correlations between therapy parameter values and patient parameter values that are discussed above. These correlations are formed using the values recorded during the data collection phase. This table is used to facilitate closed-loop operation during data validation.

In another embodiment, the IMD develops the table of data used to facilitate closed-loop operation at the start of the data validation phase. In particular, the table is populated using therapy parameter values that are provided to the IMD from data collected during the data collection phase. These values may be communicated to the IMD via an automated programmer that operates under the control of controls scripts. Once so populated, this table is used by the IMD to control the closed-loop operation during the data validation phase.

As discussed above, during the validation phase, the automated device is automatically re-creating a sequence of conditions (e.g., postures and/or activity states) that occurred during the data collection phase. This is done by providing the patient parameter values collected from the externally-worn sensor to the automated device. According to another aspect of the disclosure, a technique is provided to verify that this recreation is occurring accurately. This involves affixing a sensor to the automated device that is the same as, or similar to, that used as the external sensor during data collection. This sensor may be calibrated such that a predetermined sensor reading is obtained when the automated device is generating a corresponding calibration condition (e.g., is oriented in a predetermined manner and/or moving in a predetermined manner). Once so affixed and calibrated, the patient parameter data collected during the collection phase may be used to control the automated device. When this occurs, the sensor affixed to the automated device detects a sequence of patient parameter values describing the re-created sequence of conditions. This sequence of patient parameter values obtained while re-creating the sequence of conditions (e.g., the posture state transitions) is compared to the sequence of patient parameter values used to control the automated device. The two sequences should be approximately the same. Significant discrepancies may indicate a design problem with control of the automated device. Such problems must be resolved prior to performing validation of the medical device in the manner described above.

It will be recognized that while one embodiment of the disclosed mechanisms that is described in detail below relates to the delivery of electrical stimulation therapy, other embodiments are possible. For instance, the disclosed mechanism may be used to validate a device that delivers a drug or other substance to a body in a manner that changes based on conditions to which an IMD is subjected. The disclosure may likewise be used to validate any other type of IMD that delivers another type of therapy, including light, motion, and/or sound in a closed-loop manner.

FIG. 1 is a conceptual diagram illustrating an example system 10 that facilitates closed-loop therapy adjustment. In the illustrated example, system 10 includes an IMD 12, which is implanted within, and delivers neurostimulation therapy to, patient 14. In exemplary embodiments, IMD 12 takes the form of an implantable pulse generator, and delivers neurostimulation therapy to patient 14 in the form of electrical pulses. It will be understood that IMDs configured in a manner other than that shown in FIG. 1 and/or that deliver other types of therapy may be usefully employed with the validation techniques described herein, and FIG. 1 is merely exemplary.

IMD 12 delivers neurostimulation therapy to patient 14 via leads 16A and 16B (collectively "leads 16"). Leads 16 may, as shown in FIG. 1, be implanted proximate to the spinal cord 18 of patient 14, and IMD 12 may deliver SCS therapy to patient 14 in order to, for example, reduce pain experienced by patient 14. In other configurations, one or more leads 16 may extend from IMD 12 to the brain (not shown) of patient 14, and IMD 12 may deliver deep brain stimulation (DBS) therapy to patient 14 to, for example, treat tremor, Parkinson's disease, or epilepsy. As further examples, one or more leads 16 may be implanted proximate to the pelvic nerves (not shown), stomach (not shown), or sexual organs (not shown) and IMD 12 may deliver neurostimulation therapy to treat incontinence, gastroparesis, or sexual dysfunction. IMD 12 may additionally or alternatively be coupled to one or more catheters to deliver one or more therapeutic substances to patient 14, e.g., one or more drugs.

In exemplary embodiments, IMD 12 delivers therapy according to one or more programs. A program includes one or more parameters that define an aspect of the therapy delivered by the medical device according to that program. For example, a program that controls delivery of stimulation by IMD 12 in the form of pulses may define a voltage or current pulse amplitude, a pulse width, a pulse shape, an electric field and/or a pulse rate, used to deliver energy to tissue according to that program. Further, each of leads 16 may carry electrodes (not shown in FIG. 1), and the parameters for a program that controls delivery of stimulation therapy by IMD 12 may include information identifying which electrodes have been selected for delivery of pulses according to the program, and the polarities of the selected electrodes, i.e., the electrode configuration for the program. Programs that control delivery of other therapies by IMD 12 may include other parameters. For example, a program that controls delivery of a drug or other therapeutic agent may include a titration rate or information controlling the timing and/or size of bolus deliveries.

As discussed above, in one embodiment, IMD 12 may deliver therapy to patient 14 according to therapy information within a record. A plurality of records may be stored in a table or other data structure. This structure may be continually updated as associations are formed between therapy information (e.g., therapy parameter values) and patient parameter values during a "learning" process. Each record includes at least one sensed patient parameter value (e.g., a sensed value that indicates patient posture or activity). This value may be associated therapy information. The therapy information may comprise a complete program that IMD 12 uses to deliver therapy, one or more therapy parameter values, or absolute or percentage adjustments for one or more parameters. When IMD 12 later detects a value of a patient parameter that was previously stored and associated with a therapy adjustment, IMD 12 may automatically adjust therapy as indicated by the therapy information in the record for the patient parameter value, e.g., by delivering therapy according to the program in the record, or by adjusting one or more parameters as indicated by the therapy information in the record.

In the illustrated example, system 10 also includes a programming device 20, which may, as shown in FIG. 1, be a handheld computing device. Programming device 20 allows a user to interact with IMD 12. Programming device 20 may, for example, communicate via wireless communication with IMD 12 using radio-frequency (RF) telemetry techniques, or any other techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude.

In exemplary embodiments, programming device 20 is a patient programmer used by patient 14 to control the delivery of neurostimulation therapy by IMD 12. Patient 14 may use programming device 20 to activate or deactivate, e.g., start or stop, neurostimulation therapy. Patient 14 may also use programming device 20 to adjust the therapy. For example, a patient may use programming device 20 to select one or more programs from among a plurality of stored programs. The selected program is then used by IMD 12 to deliver therapy. This may occur, for example, when patient 14 switches from one program to another using programming device 20. The programs may be stored by IMD 12 or patient programmer 20. Further, patient 14 may also use programming device 20 to adjust therapy by adjusting one or more stimulation parameters such as, but not limited to, the amplitude, width, rate, field shape, pulse shape, and/or duty cycle of delivered stimulation for the one or more programs.

Patient 14 may provide a number of consecutive inputs to adjust the therapy information. These consecutive inputs may be described singly as a "therapy adjustment." Programming device 20 and IMD 12 may treat all consecutive inputs as an adjustment before acting on the changes. Each input may only be separated by a pre-defined time delay, or all inputs may occur within a predefined time period, to treat the inputs as one adjustment. When patient 14 adjusts one or more stimulation parameters, and/or switches programs, IMD 12 detects a value of a sensed patient parameter, and associates therapy information with the detected value. In some embodiments, IMD 12 stores the associated parameter value and therapy information as a record within a table or other data structure. This type of information may subsequently be used to control IMD 12 in a closed-loop manner. If an existing record already contains the same patient parameter value as is currently sensed by the system, IMD 12 may modify the existing record to include new therapy information based on the patient adjustment. Otherwise, IMD 12 may add a new record with the associated patient parameter value and therapy information.

In some embodiments, the data structure containing the above-described associations may be maintained by, and stored in, programming device 20 instead of IMD 12. Accordingly, one or both of IMD 12 and programming device 20 may provide closed-loop adjustment of the therapy delivered by IMD 12. In embodiments in which programming device 20 maintains the data structure, the programming device may receive therapy adjustments from patient 14 via user interface components such as display 22 and keypad 24. In such embodiments, programming device 20 may include sensors that sense the patient parameter, or may receive values of the patient parameter from IMD 12. Programming device 20 may send commands to IMD 12 based on therapy information stored in the data structure to effect closed-loop delivery of therapy.

In response to receiving a therapy adjustment from patient 14, e.g., via programming device 20, IMD 12 detects a value of a sensed patient parameter, and associates therapy information with the value. The sensed parameter value may be an activity and/or posture of patient 14, and the therapy information may include the therapy parameters currently used, or adjustments to such parameters made, at the time the sensed patient parameter value was detected. In exemplary embodiments, IMD 12 continually "learns" such associations, e.g., by updating the applicable table or other data structure. Closed-loop delivery of therapy by IMD 12 based on the associations of therapy information with sensed patient parameter values may eventually eliminate the need for patient 14 to manually adjust therapy parameters.

For example, patient 14 may adjust the amplitude of stimulation, which may indicate that the original program was inadequate to treat the patient because of a change of symptoms. The change in symptoms may be correlated with a change in a sensed patient parameter. For example, both of these changes may be due to the patient undertaking an activity or posture, such as running, golfing, taking medication, sleeping, sitting, bending over, transitioning from sitting to standing, or some particular activity or posture related to an occupation of patient 14. IMD 12 may associate therapy information determined based on the received therapy adjustment with a value of a patient parameter, e.g., an activity, activity level, or posture, that is sensed at the time of the therapy adjustment by a sensor.

In some embodiments, a user other than patient 14 may user programmer 20, or another programming device that may or may not be associated with patient 14, to adjust therapy for patient. The therapy adjustments made by another user may result in updating the table or other data structure with a new or modified association of a therapy parameter value with a patient parameter value.

Further, in some embodiments, IMD 12 may also monitor the sensed patient parameter, and create additional associations between patient parameter values and existing therapy information, without receiving any therapy adjustment from patient 14. In particular, when the sensed patient parameter value has changed without a therapy adjustment, IMD 12 may automatically associate the patient parameter value with therapy information determined based on the current, unadjusted therapy parameters. In some embodiments, IMD 12 may only make such an automatic, non-adjustment based association if the sensed patient parameter value has changed by a threshold or "resolution" value, which may be for example an absolute or percentage value.

The resolution value for the sensed patient parameter may control the size and resolution of a data structure that stores associations between values of the patient parameter and therapy information; whether the associations are made based on a therapy adjustment or not. The resolution value may be set by, for example, by a manufacturer of IMD 12 or a clinician, and controls difference in the parameter value that IMD 12 identifies as being significant enough to update the data structure. If the resolution value is set to a high value, the data structure may include a greater number of records, each with respective values for the patient parameter. A high resolution value may accordingly provide more stimulation control. Alternatively, the resolution value may be set to a low value to limit the number of records in the data structure, which would also result in less frequent therapy adjustments. In some embodiments, IMD 12 may increase the resolution value if existing records are frequently being modified or overwritten, e.g., in response to frequent therapy adjustments by the patient or other user. This occurrence may indicate that patient 12 or other user needs a higher level of control of adjustments to stimulation therapy.

A sensor used to sense patient parameters may be implanted at a site within patient 14, worn on the exterior of the patient, or located within IMD 12. An example sensor is a three-axis accelerometer located within IMD 12. Patient parameter values detected by IMD 12 based on the signals generated by such a sensor may correspond to an activity and/or posture undertaken by patient 14. Signals related to activity may describe a gross level of physical activity such as activity counts based on footfalls or the like, an activity vector in three-dimensional space indicating direction of velocity or acceleration, etc.

As one example, a three-axis accelerometer may provide a signal that includes both a DC and an AC component. The DC component indicates the orientation of the accelerometer within the earth's gravitation field. Assuming the accelerometer is in a fixed known position in relation to the patient's body, the DC component of the accelerometer measurement may be used to determine a posture of a patient. In particular, the DC component of the accelerometer may be expressed as a vector in three-dimensional space. By comparing this vector to vectors that have been used to define known postures, a patient's posture may be classified as one of the known postures, or alternatively classified as being "not classified".

Similarly, a signal provided by an accelerometer may also include an AC component that may be used to determine and classify a patient's activity, including the activity level, velocity and/or acceleration of the patient's motion, a direction of the velocity and/or direction of acceleration associated with the motion, etc.

In this manner, a three-axis accelerometer signal may be used to classify a patient's posture state as well as changes in that posture state, where a posture state includes at least one of a posture and an activity level parameter. Techniques for detecting and classifying posture states are described in commonly-assigned patent applications entitled "Posture State Classification for a Medical Device", Ser. Nos. 12/433,004 and 12/432,993 both filed Apr. 30, 2009, incorporated herein by reference in their entireties.

As an example of use of a three-axis accelerometer signal, IMD 12 may record the accelerometer signal, which is then associated with a therapy adjustment that is received contemporaneously with receipt of the accelerometer signal. When IMD 12 later detects the same output from the accelerometer, e.g., when patient 14 is again in a same position as when the signal was recorded, IMD 12 may automatically deliver therapy appropriate for that position.

By providing therapy adjustments automatically, IMD 12 may allow patient 14 to avoid having to manually adjust the therapy each time a particular patient parameter value occurs, e.g., each time the patient engages in a particular activity, activity level or posture. Such manual adjustment of stimulation parameters can be tedious, requiring patient 14 to, for example, depress one or more keys of keypad 24 multiple times during the patient activity to maintain adequate symptom control. Instead, when closed-loop therapy is delivered, patient 14 may eventually need to manually adjust stimulation therapy rarely, if at all, once IMD 12 has compiled a comprehensive program table.

As may be appreciated, the automated delivery of therapy in a closed-loop manner must, at some point, be validated. This validation process is necessary to ensure that therapy selected by the patient is indeed being delivered in response to detected conditions that are the same as those recorded during a learning period. Generally, this type of validation may be performed during design testing and implementation. As discussed in detail below, techniques are provided for automatically performing this validation in a manner that is accurate, efficient, cost effective, and reproducible.

Figure 2:
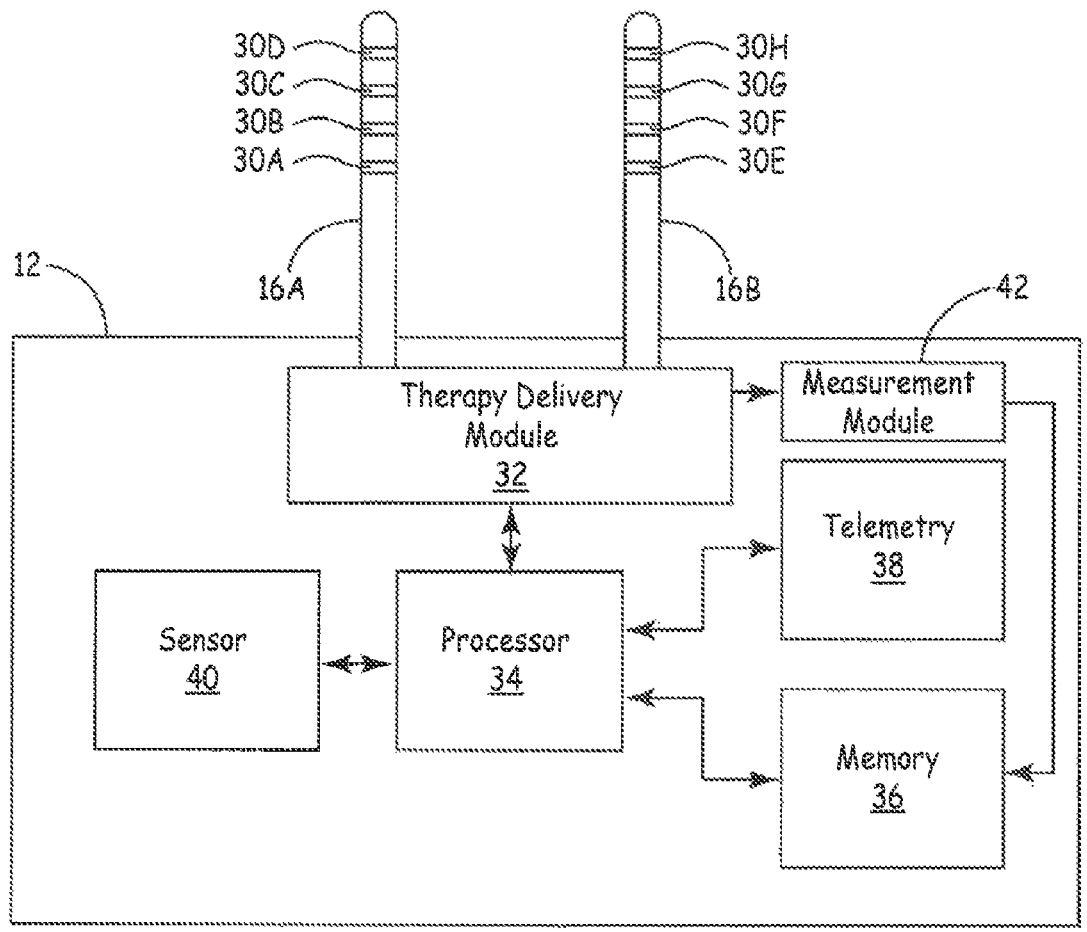
FIG. 2 is a block diagram illustrating an example medical device that delivers therapy and provides closed-loop adjustment of the therapy.

FIG. 2 is a block diagram illustrating IMD 12 in greater detail. IMD 12 may deliver neurostimulation therapy via electrodes 30A-D of lead 16A and electrodes 30E-H of lead 16B (collectively "electrodes 30"). Electrodes 30 may be ring electrodes or some other type of electrodes. The configuration, type and number of electrodes 30 illustrated in FIG. 2 are merely exemplary. For example, IMD 12 may be coupled to one lead with eight, or some other number, of electrodes on the lead. Alternatively, IMD 12 may be coupled to more than two leads.

Electrodes 30 are electrically coupled via leads 16 to a therapy delivery module 32, which may be a stimulation pulse generator. Therapy delivery module 32 may, for example, include an output pulse generator coupled to a power source such as a battery. Therapy delivery module 32 may deliver electrical pulses to patient 14 via at least some of electrodes 30 under the control of a processor 34.

Processor 34 may control therapy delivery module 32 to deliver neurostimulation therapy according to a selected program. Specifically, processor 34 may control therapy delivery module 32 to deliver electrical pulses with the amplitudes and widths, and at the rates specified by the program. Processor 34 may also control therapy delivery module 32 to deliver the pulses via a selected subset of electrodes 30 with selected polarities, e.g., a selected electrode configuration, as specified by the program.

Processor 34 may also control therapy delivery module 32 to deliver the neurostimulation therapy according to records stored within a table or other data structure, as described above. Processor 34 may create and modify this table during a learning period, and at time thereafter as determined by a closed-loop therapy delivery algorithm. Specifically, processor 34 may receive a therapy adjustment from a user, such as patient 14, detect a patient parameter value, and associate therapy information with the patient parameter value by creating or modifying a record within the data structure, as described above.

Processor 34 may subsequently detect previously-recorded patient parameter values, and control therapy delivery module 32 to deliver therapy via at least some of electrodes 30 as indicated by the associated therapy information. For example, processor 34 may control therapy delivery module 32 to deliver stimulation pulses with the amplitude, width, rate, shape, and/or electrode configuration indicated by the therapy information, or, in some embodiments, may control therapy delivery module 32 to adjust the amplitude, width, and/or rate over time as indicated by the therapy information.

IMD 12 may also include a telemetry circuit 38 that allows processor 34 to communicate with programming device 20. Processor 34 may receive program selections, therapy parameter adjustments, or other therapy adjustments, as well as commands to initiate or terminate stimulation, from a user, e.g., patient 14. This information may be received from programming device 20 via telemetry circuit 38.

In some embodiments, processor 34 also communicates with a clinician programmer to provide diagnostic information and validation data stored in memory 36 to a clinician via telemetry circuit 38. The clinician programmer may operate similarly to programmer 20, but the clinician programmer may be more fully featured, e.g., provide greater control of or interaction with IMD 12, than programming device 20. Telemetry circuit 38 may correspond to any telemetry circuit known in the implantable medical device arts.

In exemplary embodiments, as described above, IMD 12 includes at least one sensor 40 that senses a patient parameter.

Processor 34 detects values of a patient parameter based on one or more signals generated by sensor 40. Sensor 40 may be a sensor that generates an output based on activity (activity level and/or direction), posture, and/or one or more physiological parameters of patient 14, as discussed above. In exemplary embodiments, sensor 40 is a three-axis accelerometer, such as a piezoelectric and/or micro-electro-mechanical accelerometer. In other embodiments, a single-axis accelerometer may be employed, or multiple single-axis accelerometers may be used in place of one three-axis accelerometer. For instance, IMD 12 may include multiple sensors oriented along various axes.

In some embodiments, processor 34 processes the analog output of sensor 40 to determine activity and/or posture information. For example, where sensor 40 comprises a micro-electro-mechanical accelerometer, processor 34 may process an AC component of the raw signal provided by sensor 40 to determine activity counts of the system, which may be indicative of footfalls, for instance. As another example, processor 34 may process the AC signal component to determine velocity or acceleration of motion along one or more axis. A DC component of the sensor signal may be used to derive posture, as discussed above.

Although illustrated in FIG. 2 as including a single sensor 40, other configurations may include any number of sensors (hereinafter "sensor 40"). Moreover, in exemplary embodiments, sensor 40 is housed within a housing (not shown) of IMD 12. In other configurations, one or more sensors may be coupled to IMD 12 via additional leads 16 (not shown). Such sensors may be located anywhere within patient 14. For instance, IMD 12 may be coupled to multiple accelerometer sensors located at various positions within patient 14 or on the external surface of patient 14, and processor 34 may receive more detailed information about the posture and/or activity undertaken by patient 14. For example, accelerometer sensors may be located within the torso and at a position within a limb, e.g., a leg, of patient 14.

Sensor 40 may communicate wirelessly with IMD 12 instead of requiring a physical connection with the IMD. For example, a sensor located external to patient 12 may communicate wirelessly with processor 34, either directly or via programming device 20. In some embodiments, one or more sensors may be included as part of or coupled to programming device 20.

The exemplary system of FIG. 2 further includes processor 34, which may comprise a microprocessor, a controller, a digital signal processor (DSP), an application specific integrated circuit (ASIC), a field-programmable gate array (FPGA), discrete logic circuitry, or the like. IMD 12 also includes a memory 36, which may include programmed instructions that, when executed by processor 34, cause IMD 12 to perform the functions ascribed to IMD 12 herein. Memory 36 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like.

IMD 12 may further include a measurement module 42 to determine the therapy that is being delivered by therapy delivery module 32. For instance, measurement module 42 may be used to record amplitude, frequency, duty cycle, shape, the field generated, electrode usage, and other parameters associated with therapy delivery. Such measurement may be performed by voltage and/or current detection circuits, A/D converters, and other logic circuits used to detect and digitize electrical signals. Additionally or alternatively, measurement module 42 may include circuits for reading registers of therapy delivery module 32 to determine how therapy is being delivered by therapy delivery module 42. These measured and/or retrieved values may be recorded within memory 36 and provided by telemetry circuit 38 to an external device such as a clinician or laboratory programmer in a manner to be discussed below.

Figure 3:
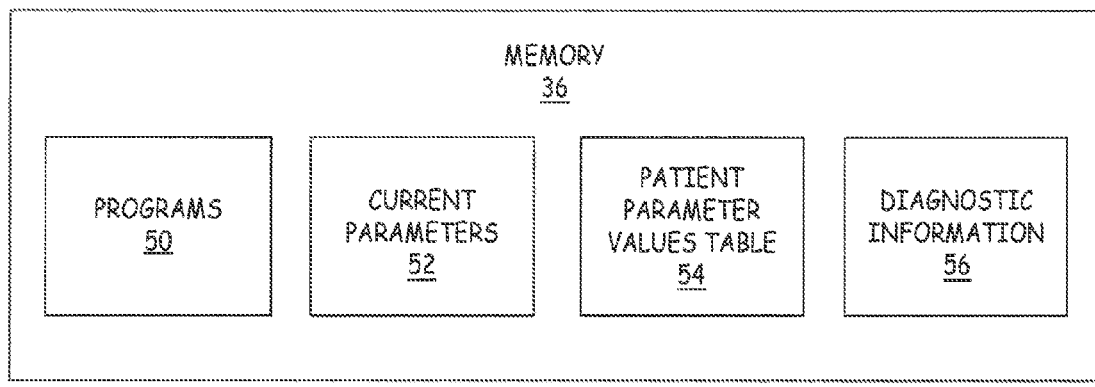
FIG. 3 is a block diagram illustrating an example configuration of a memory of the medical device of FIG. 2.

FIG. 3 is a block diagram illustrating an exemplary configuration of memory 36 of IMD 12. As illustrated in FIG. 3, memory 36 stores programs 50, one or more of which processor 34 (FIG. 2) may select to control delivery of stimulation by therapy delivery module 32, as described above. Each of the programs includes respective values for a plurality of therapy parameters, such as pulse amplitude, pulse width, pulse rate, and electrode configuration, as described above. Processor 34 may select one or more programs based on input or commands received from patient 14 via programming device 20 and telemetry circuit 38. Programs 50 may have been generated using a clinician programmer, e.g., during an initial or follow-up programming session, and received by processor 34 from the clinician programmer via telemetry circuitry 38. In other embodiments, programming device 20 stores programs 50, and processor 34 receives selected programs from programming device 20 via telemetry circuit 38.

In some embodiments, memory 36 also stores an indication of the current therapy parameters 52 used by processor 34 to control delivery of stimulation by therapy delivery module 32. Current therapy parameters 52 may identify the one or more selected programs, or may reflect modifications to one or more therapy parameters of the one or more programs based on patient adjustment. Further, processor 34 may determine current therapy parameters 52 based on therapy information associated with a detected value of a sensed patient parameter, as described herein.

As described above, patient parameter values table 54 comprises a plurality of records that each includes at least one respective value of a patient parameter and associated therapy information. When therapy is first initiated, table 54 may be empty. As therapy progresses during a learning phase, processor 34 creates records, by associating therapy information with patient parameter values, and stores them in table 54. If a therapy adjustment causes processor 34 to identify a sensed patient parameter value that is substantially identical to, or within an allowable tolerance of, a patient parameter value for an existing record, processor 34 modifies the existing record based on new therapy information in order to keep updated therapy information available for stimulation therapy. In this manner, IMD 12 is capable of adapting to changes in patient physiology during the therapy. For instance, patient parameter values stored in table 54 may include the raw output of sensor 40, which may be an accelerometer. Additionally, or alternatively, the parameter values could include processed signal data obtained via hardware processing, software processing, or some combination thereof. If the sensor is an accelerometer, the processed signal data may include an AC signal component, a DC signal component, a posture classification, an activity level, and/or some other indication of activity of the patient.

Processor 34 may also collect diagnostic information 56 that is then stored within memory 36 for future retrieval by a clinician. Diagnostic information 56 may, for example, include selected recordings of the output of sensor 40 and/or of therapy changes made by patient 14. In exemplary embodiments, diagnostic information 56 may include information identifying the time at which patient sensor outputs occurred. Diagnostic information 56 may include other information or activities indicated by patient 14 using programming device 20, such as changes in symptoms, taking medication, or other activities undertaken by patient 14.

A clinician programming device (not shown in the figures) may present diagnostic information 56 to a clinician in a variety of forms, such as timing diagrams, or a graph resulting from statistical analysis of diagnostic information 56, e.g., a bar graph. Diagnostic information 56 may also include calibration routines for sensor 40 and malfunction algorithms to identify stimulation or control dysfunctions.

Figure 4:
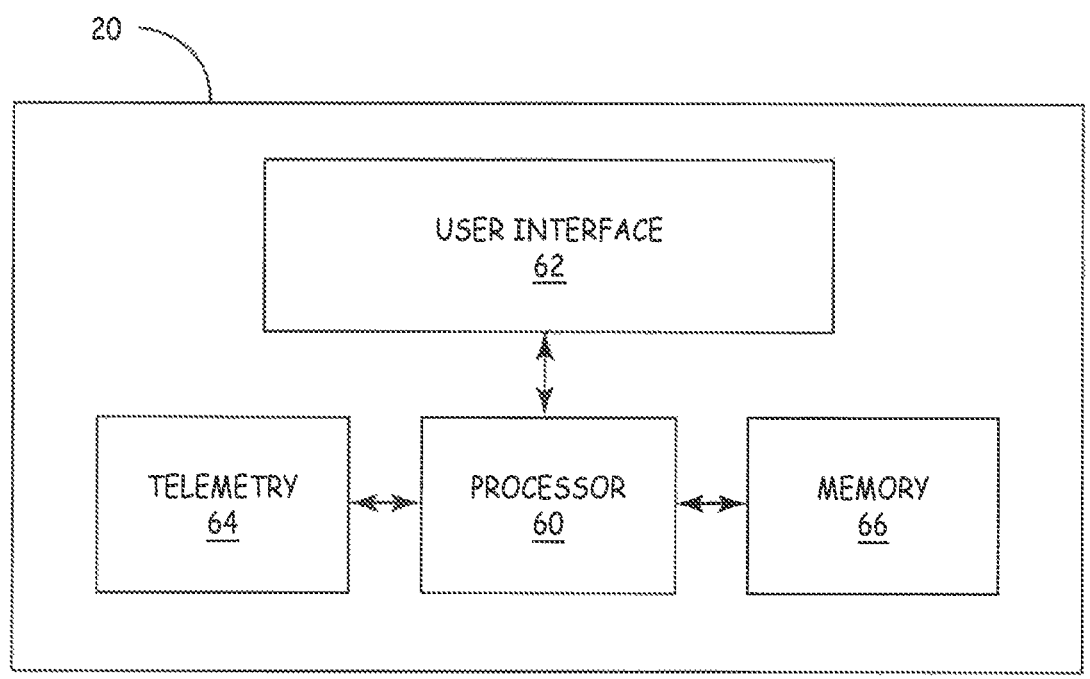
FIG. 4 is a block diagram illustrating an example external programmer that allows a patient to communicate with the medical device of FIG. 2.

FIG. 4 is a block diagram further illustrating programming device 20. As indicated above, in exemplary embodiments programming device 20 takes the form of a patient programming device used by patient 14 to control delivery of therapy by IMD 12. Patient 14 may interact with a processor 60 via a user interface 62 in order to control delivery of neurostimulation therapy, e.g., provide patient therapy adjustments, as described herein. User interface 62 may include display 22 and keypad 24, and may also include a touch screen or peripheral pointing devices as described above. Keypad 24 may include an increase amplitude button and a decrease amplitude button. Processor 60 may also provide a graphical user interface (GUI) to facilitate interaction with patient 14. Processor 60 may include a microprocessor, a controller, a DSP, an ASIC, an FPGA, discrete logic circuitry, or the like.

Programming device 20 also includes a telemetry circuit 64 that allows processor 60 to communicate with IMD 12. In exemplary embodiments, processor 60 communicates commands, indications, and therapy adjustments made by patient 14 via user interface 62 to IMD 12 via telemetry circuit 64. Telemetry circuit 64 may correspond to any telemetry circuit known in the implantable medical device arts.

Programming device 20 also includes a memory 66. In some embodiments, memory 66, rather than memory 36 of IMD 12, may store programs 50 and table 54 to control delivery of neurostimulation therapy. Memory 66 may also include program instructions that, when executed by processor 60, cause programming device 20 to perform the functions ascribed to programming device 20 herein. Memory 66 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 5:
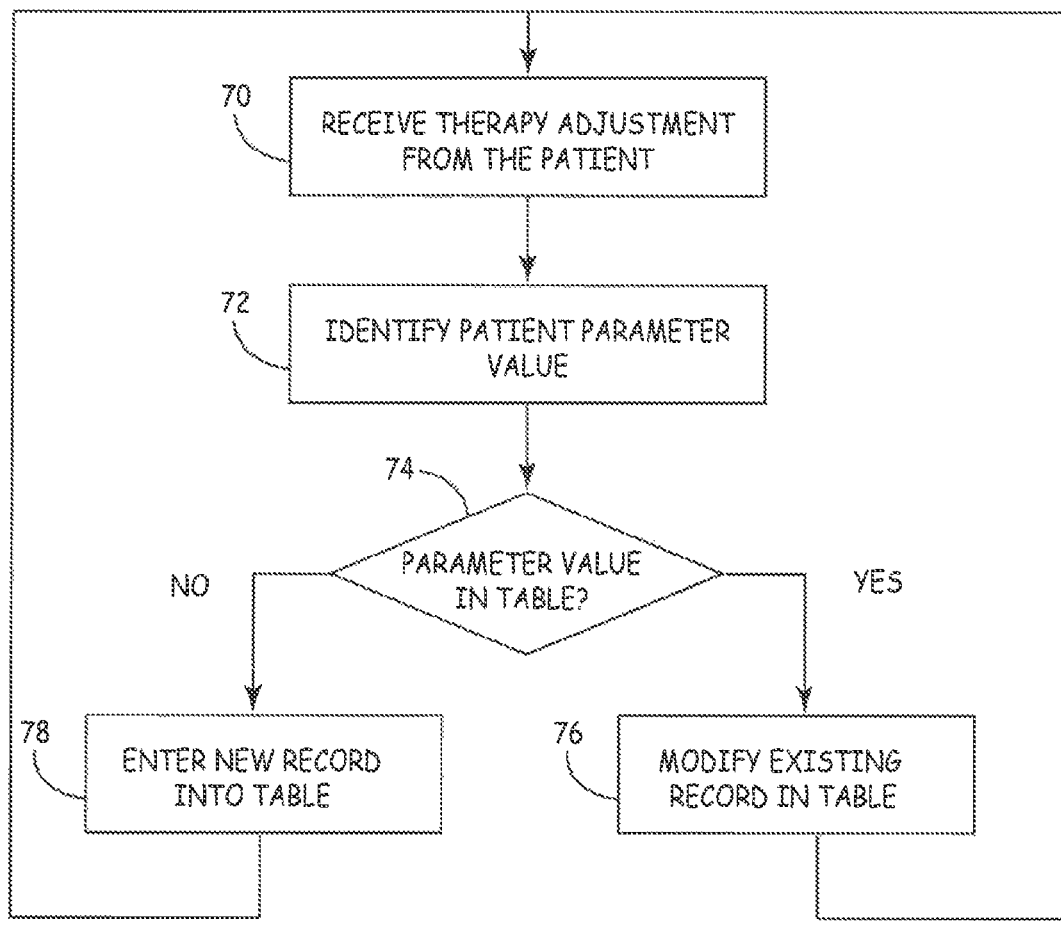
FIG. 5 is a flow diagram illustrating an example technique for automatically associating therapy information with patient parameter values in response to therapy adjustments.

FIG. 5 is a flow diagram illustrating an example technique for automatically associating therapy information with patient parameter values in response to patient therapy adjustments. More particularly, FIG. 5 illustrates an example technique for updating a program table following therapy adjustments by patient 14. The illustrated technique may be performed by a medical device, such as IMD 12, and will be described with reference to IMD 12 and system 10.

During therapy, processor 34 of IMD 12 receives a therapy adjustment from patient 14 via programmer 20, e.g., an amplitude adjustment (70). Processor 34 determines therapy information, such as the amount or percentage of the amplitude adjustment, the adjusted value of the amplitude, or respective values for a plurality of therapy parameters including the adjusted amplitude value, based on the therapy adjustment. Processor 34 also identifies a current value of a patient parameter, such as posture or activity, based on a signal generated by sensor 40 (72).

Processor 34 determines whether any of the records in table 54 already include or encompass the identified patient parameter value (74). If the patient parameter value is already in an existing record of table 54, processor 34 modifies, or in some cases, adds to, the existing record based on the newly determined therapy information (76). Otherwise, processor 34 may enter a new record including the identified patient parameter value and the determined therapy information into the table 54 (78). The determination of whether a value of the sensed patient parameter is included in or encompassed by a record already in table 54, e.g., whether the value is substantially equivalent to an existing value, may depend on the resolution value for the sensed parameter, which was discussed above with reference to FIG. 1.

In some cases, the therapy adjustment received from patient 14 may be one or more inputs or a command that stops delivery of therapy. Such an adjustment indicates that the current therapy parameter values 52, whether they were determined based on a program 50 or therapy information from table 54, were inappropriate for the current condition of patient 14. The current condition of the patient is reflected by the current value of a sensed patient parameter. As an example, the patient may stop therapy if it becomes too intense when a particular posture such as lying down is assumed.

In response to such a therapy adjustment, processor 34 may remove any current association between the current value of the sensed patient parameter and therapy information, e.g., delete any record in table 54 for the current value of the sensed patient parameter. In this manner, the next time patient 14 assumes a problematic posture or activity, no change in therapy from whatever therapy is currently being delivered will occur. As another alternative, in this type of situation, processor 34 may instead create a new record or modify an existing record such that a relatively innocuous, predetermined therapy program is associated with the patient parameter value that indicates the problematic condition, e.g., posture or activity, of the patient.

Alternatively, processor 34 or programming device 20 may request patient 14 to assume the activity or posture associated with the therapy discontinuation, and manually find therapy parameters that provide comfortable and efficacious therapy. In this case, processor 34 or the programming device may provide some guidance or direction to patient 14 to assist in quickly determining therapy parameters that are effective. Once such parameter values are found, IMD 12 may create a record in table 54 that associates the previously problematic sensed patient parameter value with the therapy information chosen by patient 14.

Part of the learning process may involve monitoring therapy adjustments over a relatively long period of time. Using averaging or some other processing method, base-level therapy parameters may be derived that reflect an average level of therapy generally desired by a patient in a given situation (e.g., when transitioning from a prone to a sitting position) as determined by the patient parameter values. In addition to this base-level therapy parameter, one or more short-term adjustments may also be associated with this same posture transition, and may be used to adjust therapy over a shorter predetermined period of time.

As an example of the foregoing, over a long learning period, it may be determined that a patient desires a stimulation level of approximately 1.0 V in response to detecting one or more patient parameter values indicating a transition from a prone to a sitting posture. Thus, therapy is delivered to the patient at this stimulation level as a default when this posture transition is detected. However, on a day when the patient is experiencing a higher level of pain, the patient may incrementally adjust the stimulation upward by 0.2V after this posture transition. This adjustment may be associated as a short-term adjustment with the posture transition such that during the current day, a therapy level of 1.2V will be delivered to the patient whenever the patient transitions from a prone to a sitting position. This therapy delivery continues throughout the current day unless another incremental adjustment is received from the patient during the same day that changes the adjustment value. When the next day arrives, therapy delivery resumes to the base-level of 1.0V in response to detection of the particular posture transition. Thus, it may be appreciated that in this embodiment, the IMD may be recording associations between patient parameter values and therapy values not only during an initial learning period, but also during every day use by the patient.

Once IMD 12 has "learned" the associations between sensed patient parameter values (e.g., accelerometer values) and therapy parameters that control how therapy is to be delivered, IMD may begin delivering therapy in an automated way. During this time, few, if any, patient adjustments may be needed. This type of operation is described in reference to FIG. 6.

Figure 6:
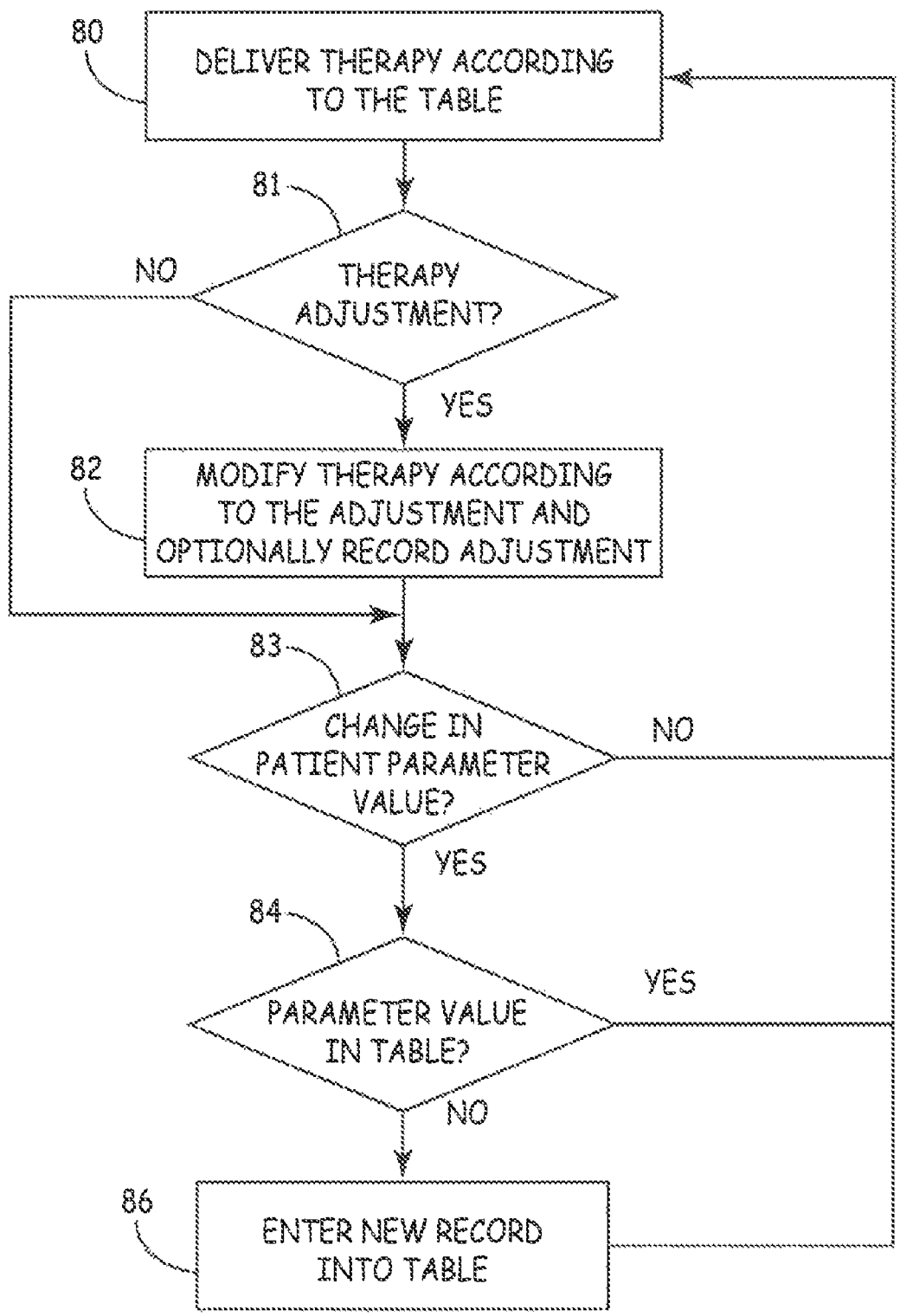
FIG. 6 is a flow diagram illustrating an example technique for delivering stimulation according to existing associations of therapy information and parameter values, and automatically associating existing therapy information with additional patient parameter values.

FIG. 6 is a flow diagram illustrating an example technique for delivering stimulation in a closed-loop manner, and further for automatically associating existing therapy information with additional patient parameter values. The illustrated technique may be performed by a medical device, such as IMD 12. Operation will be described with reference to IMD 12 and system 10. As shown in FIG. 6, processor 34 of IMD 12 controls pulse generator 32 to deliver therapy according to the therapy information stored in table 54 (80). As previously discussed, this therapy delivery may be performed using a base-level therapy value and an incremental adjustment. Processor 34 may adjust therapy parameters or change therapy programs as indicated by therapy information stored in records of table 54. Processor 34 accesses different records, and thus different therapy information, based on detected values of a sensed patient parameter, which may provide information regarding the posture and/or activity of a patient.

While therapy is being delivered according to table 54, a patient may make an incremental adjustment (81). If this occurs, the therapy that is being delivered according to the table may be adjusted accordingly (82). In one embodiment, this adjustment may be stored within table 54 for use in automatic therapy delivery either indefinitely, or for a subsequent predetermined period of time, such as during the current day.

If a therapy adjustment is not detected in step 81, therapy delivery continues until a change in a patient parameter value is detected (83). When processor 34 detects a change in the patient parameter value (83), the processor may determine whether the parameter value is already in the table (84). As discussed above, this determination may depend on a resolution value for the sensed patient parameter. If the detected patient parameter value is already in table 54, processor 34 may control therapy generator 32 to deliver therapy according to the table, e.g., according to the therapy information associated with the detected patient parameter value in the table (80). If the detected patient parameter value is not already in table 54, processor 34 may enter a new record in table 54 for the value, which associates the detected patient parameter value with the current therapy parameter values 52 (86). In this manner, processor 34 may continue to populate table 54 with therapy information for various values of therapy and/or the sensed patient parameter even after a learning period is over and the table has been put into use for providing automated therapy delivery.

In some embodiments, processor 34 may wait a predetermined time after the sensed patient parameter value changes before storing a new record. Since the output of sensor 40 may change rapidly, recording a new record for each small change in sensor output may not be necessary or even possible without slowing down the performance of processor 34. Processor 34 may wait for 10 seconds, for example, in order to let the sensor output stabilize before generating a new record.

FIG. 7 is a chart illustrating an example patient parameter value table that may be used for closed-loop adjustment of therapy. Table 110 may correspond to table 54 stored in memory 36 of IMD 12. As shown in FIG. 7, table 110 includes a plurality of records. Each record contains several values derived from an accelerometer output, which is an example of a value of a sensed patient parameter. The table further includes an amplitude, a pulse width, a pulse frequency, and an electrode configuration, which are values for example therapy parameters. Processor 34 may search table 110 based on a currently-detected accelerometer output in order to match therapy to the current condition, e.g., posture and/or activity, of patient 14.

In the current example, the accelerometer output is from a three-axis accelerometer. An AC portion of the accelerometer output may be used to derive one or more values indicative of motion of the patient, such as activity level, velocity, acceleration, and so on. In the current example, activity levels (e.g., A1-A5) are shown to be utilized, which may represent footfalls. A DC portion of the accelerometer output may be used to determine a value indicative of the orientation of the accelerometer within a gravitational field. This value may be expressed as a three-dimensional vector having X, Y, and Z components. Assuming the accelerometer position is fixed with respect to IMD 12, and the position of IMD 12 is fixed with respect to patient 14, the vector measurement may be used to determine a patient's posture.

In another embodiment, the vector may be accompanied by a tolerance, which represents some distance from the vector. For instance, the tolerance may be expressed as a cosine of an angle describes an area surrounding the vector. This area may define a cone in three-dimensional space. The vector determined from the output of an accelerometer will be matched with a table entry whenever that vector lies within the cone (assuming any activity criteria for that table entry is also satisfied). This provides a mechanism for matching any accelerometer output with one of a limited set of posture states.

According to one embodiment, if a record is not located having the same, or an applicable, activity and/or posture as is indicated by the current accelerometer output, processor 34 may enter a new record into program table 110.

Each posture state of table 110 may be associated with therapy information. Therapy information may include a voltage amplitude (as shown in the example), a current amplitude, or some other amplitude, as may be the case if a therapy other than stimulation is being provided. The current example also provides a stimulation pulse width in microseconds (µs), the pulse frequency (Hz), and the electrode configuration, which determines the electrodes and polarity used for delivery of stimulation according to the record. Other therapy parameter values may be used instead of, or in addition to, those shown in table 110.

Table 110 also illustrates the recording of an incremental adjustment, which in this example is an adjustment to the voltage amplitude. This adjustment may be received from a patient and used to adjust therapy amplitude for some predetermined period of time (e.g., the current day). When such an adjustment is received, it is entered into a table entry associated with the currently-sensed activity level and posture, and is thereafter used to adjust therapy when the patient is in that posture state. This continues until a different adjustment for this posture state is received, or until the predetermined period of time has elapsed (e.g., the next day arrives).

During system development and test of IMD 12, it is necessary to have a mechanism to validate that the IMD is indeed delivering the appropriate level of therapies, both during open-loop operation, and during closed-loop therapy delivery. The current disclosure provides techniques for performing this validation in an automated manner as described with respect to the remaining drawings.

Figure 8:
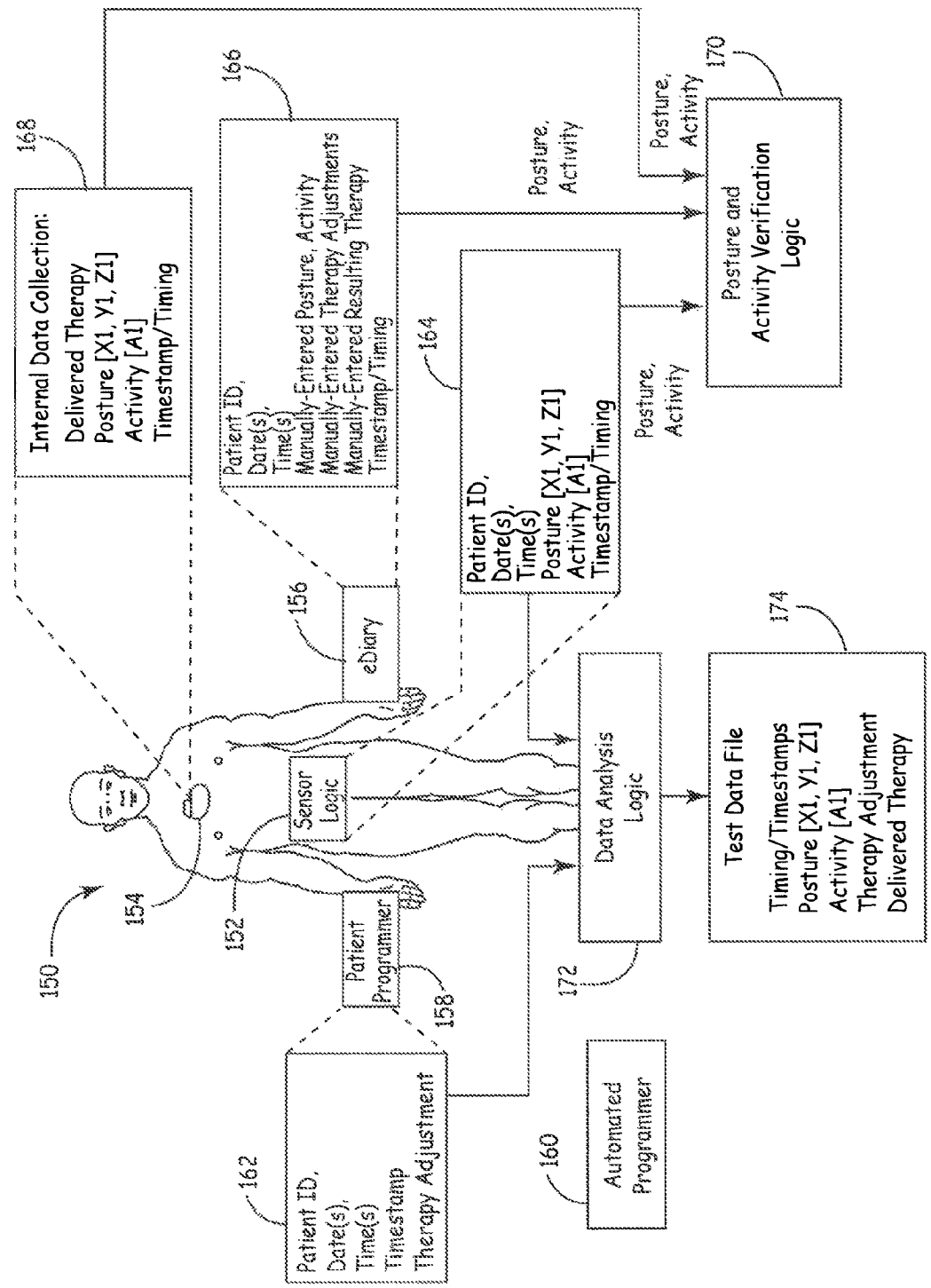
FIG. 8 is a block diagram illustrating collecting data for use in performing automated validation of an IMD according to one embodiment.

FIG. 8 is a block diagram illustrating a mechanism for performing data collection according to one embodiment. Sensor logic 152 is affixed to patient 150, as may be performed by clipping or otherwise attaching this logic in a stationary manner to an external surface of the patient or the patient's clothing. This sensor logic 152 may include a sensor such as an accelerometer discussed above. This logic may optionally further include other hardware, software, and/or firmware modules to pre-process the output of the sensor, as will be discussed below.

Sensor logic 152 may be affixed to patient 150 in a predetermined orientation. For instance, if sensor logic 152 includes a three-axis accelerometer, sensor logic may be affixed to patient 150 in a known orientation with respect to the patient. As an example, a Y axis of the accelerometer may be aligned approximately with the patient's spine and the X axis of the accelerometer may be aligned with the patient's lateral axis. Any other predetermined alignment may be used in the alternative. Alternatively, sensor logic 152 may be affixed to patient 150 and the three-axis accelerometer calibrated so that a predetermined accelerometer reading is provided when patient 150 is in a predetermined position, such as standing. Techniques for performing calibration are described in commonly-assigned U.S. patent application Ser. No. 12/433,623 filed Apr. 30, 2009, entitled "Reorientation of Patient Posture States for Posture-Responsive Therapy", incorporated herein by reference in its entirely.

Patient 150 carries an IMD 154 that delivers therapy in a known manner. For instance, IMD 154 may provide electrical stimulation therapy to the patient in a previously-verified open-loop fashion that responds to therapy modification commands from a programmer such as patient programmer 158, which may be similar to patient programmer 20 (FIG. 1).

Patient 150 uses patient programmer 158 to control the therapy delivered by IMD 154. When patient programmer 158 receives patient adjustments to modify the therapy that is being delivered by IMD, patient programmer communicates these adjustments to IMD 154, which responds accordingly to deliver the therapy in an altered manner. Patient programmer 158 may communicate such modifications via a wireless communication session such as a telemetry downlink session.

In one embodiment, patient 150 may also be provided with electronic means for manually recording conditions associated with sensor logic 152. For instance, the electronic means may be an eDiary 156 such as a personal data assistant (PDA) or other recording device for recording patient-entered data with a key pad, stylus, and/or via other user interface mechanisms.

The system of FIG. 8 further includes an automated programmer 160 (also referred to as a "lab programmer"). This programmer may be a modified clinician programmer that has a larger set of capabilities and functions than patient programmer 158. These functions include the ability to communicate with, and control IMD 154. Automated programmer 160 may be adapted for use in configuring the system of FIG. 8 for data collection. During a data validation phase that may occur after data collection is complete, automated programmer 160 is adapted to automatically issue commands that cause an IMD to adjust therapy, as will be described further below.

The various components of the system of FIG. 8 are used in concert to perform data collection as follows. First a synchronizing event is performed that synchronizes operation of patient programmer 158, sensor logic 152, eDiary 156, and optionally IMD 154. Such a synchronizing event may be a synchronization command that is selected via a user interface of an automated programmer 160, for example. Such a command may be communicated via wireless communication (e.g., telemetry) to each of the other devices, including patient programmer 158, sensor logic 152, eDiary 156, and IMD 154. Alternatively, one or more of these other devices may receive this command via a hardwired connection such as provided via a USB cable or any other type of communication connection. In one instance, some other type of signal, such as a hardwired reset signal, may be communicated to each of devices 152-158 at the same time for use as a synchronization event. In yet another embodiment, this synchronization event may alternatively or additionally involve some manual intervention, such as activating a reset switch, removing or providing a magnet that activates a configuration function, and so on.

The synchronization event is used to synchronize respective counter/timers in each of the devices 152-158. For instance, the synchronization event may zero all of the counter/timers so that clocks in each of the devices are synchronized to one another.

After the synchronization event, IMD 154 may begin delivering therapy to patient 150 according to a known manner. For instance, electronic stimulation therapy may be delivered to patient via one or more leads according to a known amplitude, frequency, electrode configuration, and so on. The way in which therapy is initially delivered may be selected according to the algorithm being executed by IMD 154 and patient programmer 158. While therapy is being delivered, therapy parameter values describing the delivered therapy are recorded by patient programmer 158. For instance, a record 162 that is created during this process may describe amplitude, frequency, duty cycle, pulse width, pulse shape, electrode combinations, electrode polarities, program usage, and so on, for the delivered electrical stimulation therapy. Each such record describing delivered therapy may be recorded along with a time stamp indicating the time at which the record was created. This time may be a relative indication, such as an elapsed time since the synchronization event occurred or a time since the last record was recorded. Alternatively, the time may be related to the time in a selected time zone. One or more of these records 162 may include additional information such as patient identification data, a date in which the record was created, and so on. Alternatively, some or all of the records may omit this type of additional information to conserve storage space.

Each record 162 may be created within a storage device of patient programmer 158, such as memory 66 (FIG. 4). Alternatively or additionally, each record 162 may be created in the memory of some other device, such as a personal computer or automated programmer 160. These records may be communicated to, and stored within, a memory of a device using wireless and/or hardwired communication link(s).

During the data collection, the patient goes about a daily routine. The patient may request adjustments to the delivered therapy. For instance, patient 150 may utilize patient programmer 158 to request incremental modifications to therapy. Such modifications may be desired because of changes in patient parameter values (e.g., changes in posture and/or activity level). For instance, the patient may want to increase stimulation levels when commencing a higher level of activity. When such therapy modification requests are received by patient programmer 158, patient programmer makes a record of the requested therapy modification. This may be recorded as some type of delta value, indicating a change between currently-delivered therapy and the therapy the patient requests. Alternatively, this may be recorded in terms of the therapy levels that will result after the modifications are applied. In either case, the recorded therapy adjustment may be stored along with a timestamp. The requested therapy modifications are communicated to the IMD 154 for use in altering delivered therapy.

While patient programmer 158 is recording therapy parameters indicative of the on-going therapy being delivered to patient 150, sensor logic 152 is sensing patient parameters indicative of a condition being experienced by the patient. For instance, assuming sensor logic 152 contains an accelerometer, sensor logic 152 records a posture state of a patient that describes at least one of a current patient position (posture) and a patient activity (e.g., activity level, velocity, acceleration, direction of the velocity, direction of acceleration, etc.) In the current example, sensor logic 152 may record patient posture using a vector in three-dimensional space as described with respect to FIG. 7. Each such record 164 containing a sensed posture state may be associated with a timestamp indicating a time of recordation. This time may be a relative time, such as time elapsed since occurrence of the synchronization event. Such records may be created within a storage device included within sensor logic 152. Alternatively or additionally, data may be provided by the sensor logic 152 to one or more other devices via a wireless or hardwired connection so that one or more such records could be created in the memory of these other devices, which may comprise a personal computer, automated programmer 160, or any other type of recording device.

Recordation of data in the foregoing manner may continue as the patient goes about daily life. During this process, sensor logic 152 will continue to monitor patient parameter values. For instance, according to the current example, the patient's posture and activity level will change, and the output of sensor logic will reflect these changes. As these posture state changes occur, patient 150 may utilize patient programmer 154 to request therapy changes. The posture state changes and the therapy changes are recorded as patient parameter values and therapy parameter values, respectively.

In conjunction with automated recordation of parameters by sensor logic 152 and patient programmer 158, patient 150 may optionally manually record data using eDiary 156. Such manual records 166 include information concerning patient parameter values. For instance, before, during, or after a posture and/or activity level change, patient 150 may manually enter data describing the change. If a posture state change is accompanied by a requested therapy modification, the patient may likewise record information describing the requested therapy change. Each such record may be associated with a timestamp in a manner similar to that associated with records 162 and 164. For instance, a timestamp may be automatically appended by the system to each record 166 each time the patient creates a new eDiary entry.

In one embodiment, IMD 154 may also be recording data associated with the delivered therapy. For instance, measurement module 42 of IMD (FIG. 2) may determine what therapy parameter values are associated with the therapy being delivered by therapy delivery module 32. Such records 168 may be stored within memory 36 of IMD 154, and/or may be transferred via a wireless communication link to a memory of automated programmer 160, a memory of a personal computer, memory 66 of patient programmer 158, or to some other storage device.

In one embodiment, IMD 154 may have a sensor 40 (FIG. 2) that is similar to that of sensor logic 152. In this case, records 168 may include patient parameter values collected by the sensor of IMD 154 (e.g., sensor 40 of FIG. 2). Such sensor is preferably of a same type and operates in a similar manner as that included within sensor logic 152. In general, it should be noted that during this phase of testing, any sensor included within IMD 154 is not being used for closed-loop control, but rather is only being used to record patient parameter values. In the current example, patient parameter values shown collected by sensor 40 of IMD 154 include posture and activity level. Records may also include a timestamp in a manner described above.

Collection of data continues in the foregoing manner, with therapy adjustments and/or a description of the resulting therapy being recorded as therapy parameter values within records 162 by patient programmer. Resulting therapy levels may also be recorded as therapy parameter values within records 168 by IMD 154 in an embodiment wherein such records are being generated. In addition to the collection of the therapy parameter values, patient parameter values as sensed by sensor logic 152 and optionally by a sensor of IMD 154 are recorded in records 164 and 168, respectively. Additional data indicative of patient parameter values and therapy parameter values may optionally be recorded manually by patient 150 as records 166 using eDiary 156. All such records may be correlated to one another via timestamps which indicate when the patient parameter values and/or therapy parameter values were recorded.

Collection of data optimally occurs as the monitored condition(s) (e.g., posture, activity level etc.) undergoes a wide variety of changes. For instance, it is desirable to perform data collection over a period of time during which a patient will experience many different postures, activity levels, and so on. In one embodiment, such monitoring continues over a period of three days, with records 162, 164, and optionally 168. Recordings may, in one instance, be created at predetermined intervals. In one embodiment, such records are created and stored every five seconds, however any other interval may be used in the alternative. Records 166 are created at intervals determined by patient compliance.

After the data collection interval (e.g., three days) has elapsed, processing of the recorded data occurs. This processing is carried out by data analysis logic 172, which forms associations between the patient parameter values (e.g., posture, activity descriptions, etc.) stored within records 164 and therapy parameter values (e.g., amplitude, frequency, etc.) stored within records 162, wherein the therapy parameter values indicate patient 150 requests to modify therapy and/or the resulting therapy delivered by IMD 154 to the patient. The associations between patient parameter values and therapy parameter values may be formed via the timestamps or according to the ordering of records that were created at known time intervals.

Data analysis logic 172 stores the created associations in a test data file 174. Test data file 74 may be retained within a storage device of automated programmer 160, a personal computer, or some other external device and/or loaded onto a storage medium such as a DVD, CD, flash drive, etc. Alternatively or additionally, this information may be transferred to a memory of a central server or some other data processing system.

If eDiary 156 is in use, processing may include an additional step to validate the operation of sensor logic 152. In particular, this step will involve validating postures and activity descriptions recorded within records 164 by sensor logic 152 against postures and activity descriptions recorded manually by patient in records 166. This validation process is performed by posture and activity validation logic 170, which may be implemented in hardware, software, or some combination thereof. In one embodiment, this logic is software executing on an external device such as automated programmer 160, a personal computer, a clinician programmer, or some other processing device.

In one example instance, posture and activity validation logic 170 operates by first assigning a posture state to the posture and/or activity data stored within each of records 164. Techniques for assigning a posture state in this manner are described in commonly-assigned patent application Ser. Nos. 12/433,004 and 12/432,993 referenced above. The assigned posture state (e.g., lying down, upright, upright & active, etc.) may then be compared to the manually-entered posture and activity data of records 166, using the timestamp data to match corresponding records. Assuming patient compliance was adequate, the resulting comparison will provide an additional level of validation indicating whether sensor logic 152 recorded data that accurately reflects patient posture and activity levels.

Optionally, a comparison may be performed between posture and/or activity data sensed by a sensor (e.g., sensor 40) of IMD, as recorded in records 168. Such data may be compared against that stored within records 164, assuming that the sensor of IMD 154 has a similar function to the sensor of sensor logic 152. Assuming it has been determined that sensor logic 152 is performing properly, this comparison may be used to confirm operation of the sensor of IMD 154 in an embodiment wherein the IMD includes such a sensor.

The foregoing describes use of timestamps to correlate data between the various ones of files 162, 164, 166, and 168. This may not be desirable in some embodiments because of the storage space required to store the timestamps. In another embodiment, records 162, 164 and 168 may be created at a same predetermined frequency (e.g., one record every five seconds). If the records of a same type are stored in an ordered manner, a correspondence will be maintained between a given record 162 and counterpart records 164 and 168. This eliminates the need to store timestamps in these types of cases. Timestamps will still generally be required in the case of records 166 which are created manually by patient 150. A record 166 may be matched with records 162, 164, and 168 by using the known data collection frequency of the automatically-collected data to select the ordered record that correlates roughly to the timestamp of a record 166.

The foregoing description of FIG. 8 relates to a system wherein during the data collection phase, all therapy delivered by IMD is provided in an open-loop manner. In other words, initially, the IMD is delivering therapy using a default set of therapy parameter values. Thereafter, therapy delivery is modified solely in response to requests made by patient 150 via patient programmer 158. No automated therapy adjustments are performed as a result of sensed patient parameter values, such as those that indicate a posture state.

In an alternative embodiment, some closed-loop control is provided by patient programmer 158 during the data collection phase. In this embodiment, sensor logic 152 and patient programmer 158 include the capability to communicate using a long-range wireless communication protocol, such as Bluetooth. Using this long-range communication protocol, the patient programmer 158 receives patient parameter values from the sensor logic 152 indicative of the patient's posture state. In this embodiment, when the patient programmer 158 receives from patient 150 a therapy adjustment, the therapy parameter values describing this therapy adjustment are stored along with patient parameter values received from the sensor logic 152 about the same time. In this manner, the patient programmer 158 creates a table that is similar to that of FIG. 7.

After patient programmer 158 has created one or more entries within the table in the manner described above, patient programmer may receive a patient parameter value that is the same as, or similar to, that already entered into this table. In this case, patient programmer 158 may automatically issue a command to adjust therapy according to the corresponding therapy parameter values include in the applicable table entry. Thus, in this embodiment, therapy adjustment occurs not only as a result of patient adjustments, but also automatically using the table values and the patient parameter values that are available from sensor logic.

During execution of this alternative embodiment, patient programmer 158 continues to create records indicative of the therapy being delivered to the patient. In this case, patient programmer 158 may also include the patient parameter values indicative of posture state in the same records as those that are recording the therapy parameter values. Thus, in this case, patient programmer 158 may create the test data file 174 directly, eliminating the need for data analysis logic 172.

In yet another embodiment, it may be desirable to pre-load patient programmer 158 with a table that associates therapy parameter values with patient parameter values. This pre-loaded table may be a default table used by many patients, or may instead contain data developed specifically for patient 150. In this case, closed-loop therapy delivery may commence immediately during the data collection phase. Updates to this table may be made as the patient makes adjustments. Patient programmer records therapy parameter values along with patient parameters in the manner described above to create test data file 174.

Figure 9:
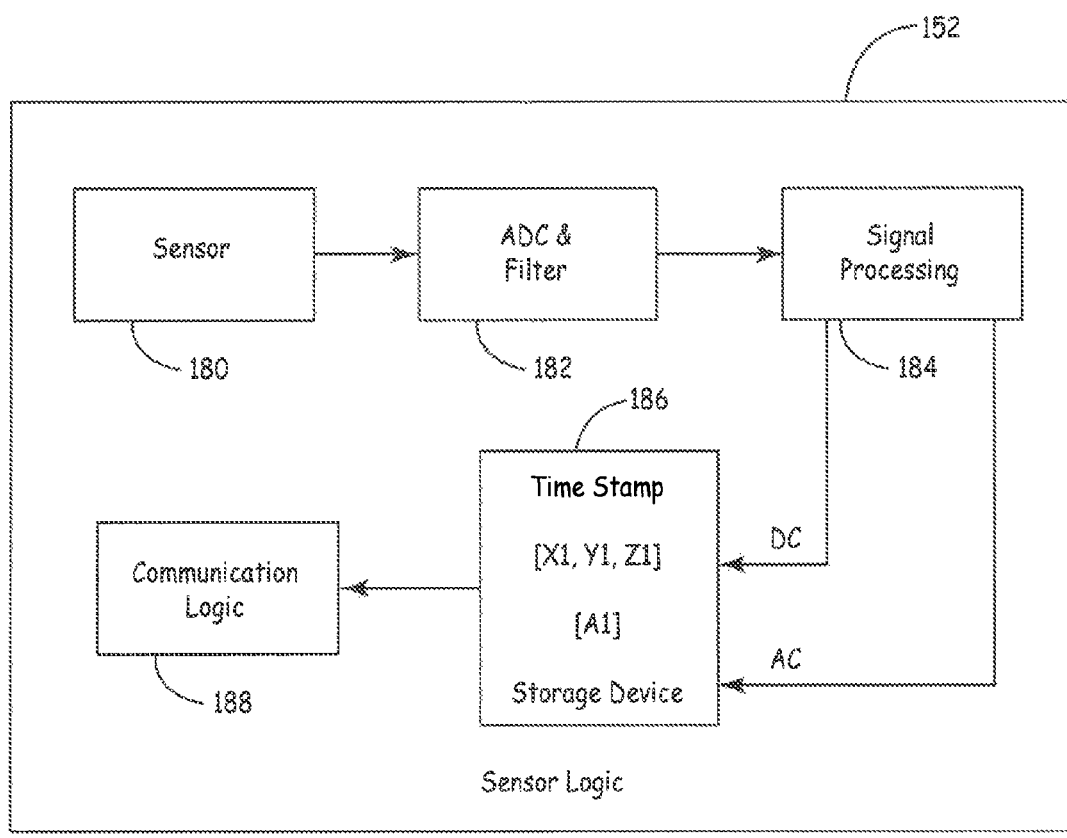
FIG. 9 is a block diagram illustrating one embodiment of sensor logic of FIG. 8.

FIG. 9 is a block diagram illustrating one embodiment of sensor logic 152. This sensor logic includes a sensor 180, which in this example may be a three-axis accelerometer. Other embodiments may be adapted for use with other types of sensors. Sensor 180 provides an output signal to logic 182, which includes analog-to-digital converter (ADC) and filter logic. When sensor 180 is an accelerometer, a high-pass filter may be used to extract an AC signal component for use in determining an activity parameter and a low-pass filter may be used to extract a DC signal component used to determine posture. Signal processing logic 184 processes both the AC and DC components to obtain a first measure indicative of posture, which in this example is a vector, and a second measure indicative of activity, which in this illustration is an activity level. Exemplary techniques for performing this signal processing are described in commonly-assigned patent application Ser. No. 12/433,029 filed Apr. 30, 2009 entitled "Posture State Detection Using Selectable System Control Parameters" referenced above.

The posture and activity level data may be stored in storage device 186 of sensor logic along with a timestamp. Alternatively, such data may be recorded at a known interval such that a timestamp may be derived in the manner discussed above. Data stored within storage device 186 may be transferred to an external device via communication logic 188, which may be a telemetry circuit capable of short-range or long-range communication. This is necessary if patient programmer 158 is to utilize closed-loop control to adjust therapy delivery according to the alternative embodiment described above. In another embodiment, communication logic 188 may simply include a communication port such as a USB or other type of connector for establishing a hardwired connection whereby data within storage device 186 may be read and used to create test data files 174 (FIG. 8).

In a scenario wherein IMD 154 automatically generates records 168 containing patient parameter values for comparison to similar values in records 164, the sensor of IMD and other logic associated with this sensor should generate values that are comparable to those generated by sensor logic 152. If this is not the case, recorded patient parameter values of records 164 will most likely not result in a favorable comparison with the patient parameter values of records 168.

Figure 10:
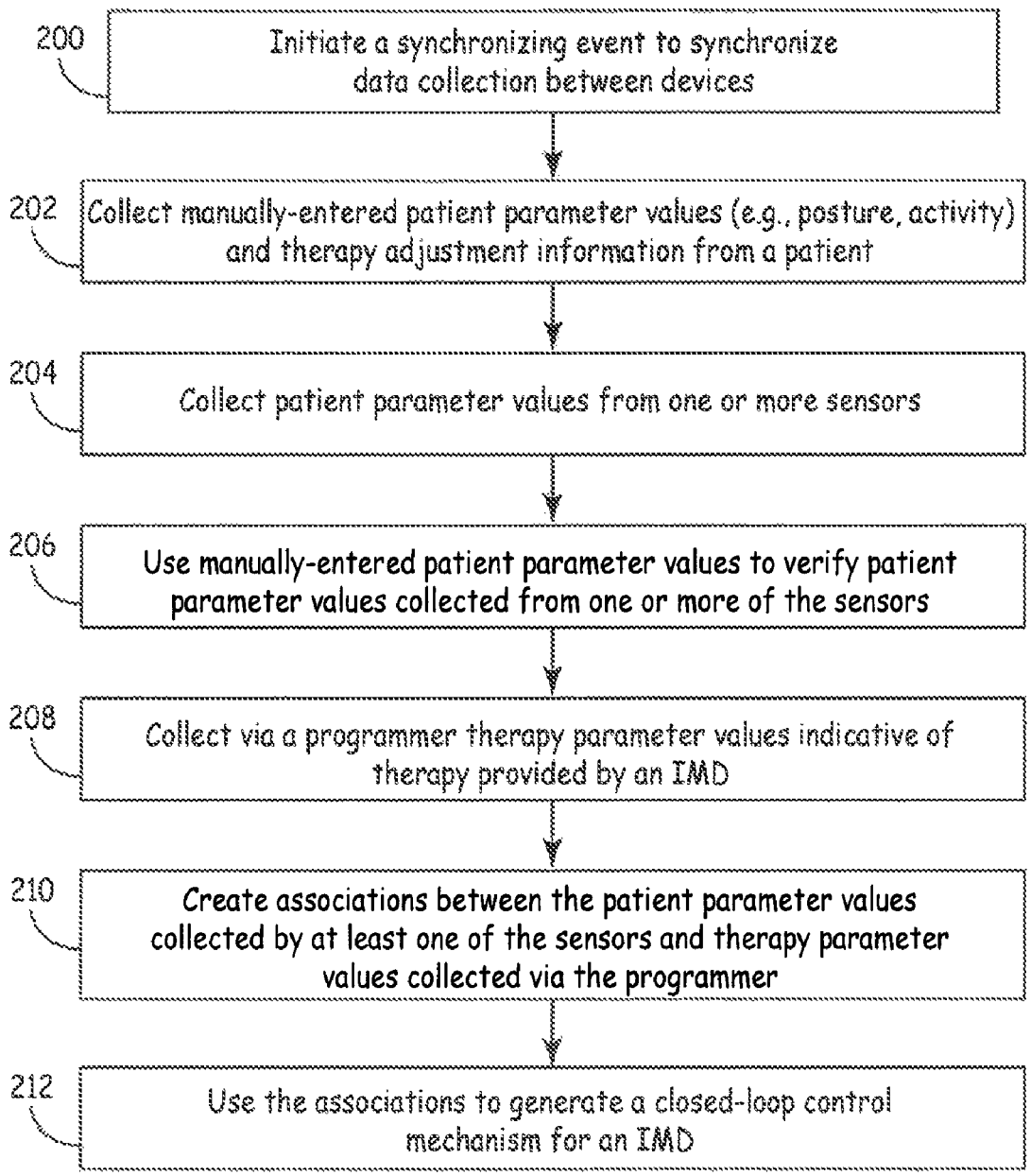
FIG. 10 is a flow diagram illustrating one method of performing data collection.

FIG. 10 is a flow diagram illustrating one method of performing data collection according to the current disclosure. A synchronizing event is initiated to synchronize the various devices performing data collection (200). During a predetermined period of time, manually-entered patient parameter values (e.g., posture, activity) and therapy parameter values may optionally be collected from a patient (202). Also during this period of time, patient parameter values are collected automatically from one or more sensors (204). These sensors include at least one sensor affixed externally to the patient. The sensors may also include a sensor of an IMD, such as sensor 40.

The manually-entered patient parameter values are optionally used to validate the raw and/or processed patient parameter values collected from the one or more sensors (206). In particular, this comparison verifies proper operation of sensor logic 152. This comparison can further validate correct operation of an internal sensor 40 and associated logic, assuming the external sensor logic 152 and the logic within the IMD correspond to one another.

Further data collection involves a programmer, which may be a patient programmer, and which is used to collect therapy parameter values indicative of therapy adjustments of an IMD (208). Associations are created between the patient parameter values collected by at least one of the sensors and therapy parameter values collected via the programmer (210), wherein the at least one of the sensors include a sensor worn externally by the patient. These associations may be stored as test data file 174 of FIG. 8. These associations are used to generate a closed-loop control mechanism to control an IMD to deliver therapy in a closed-loop manner (212), as will be discussed below.

Figure 11:
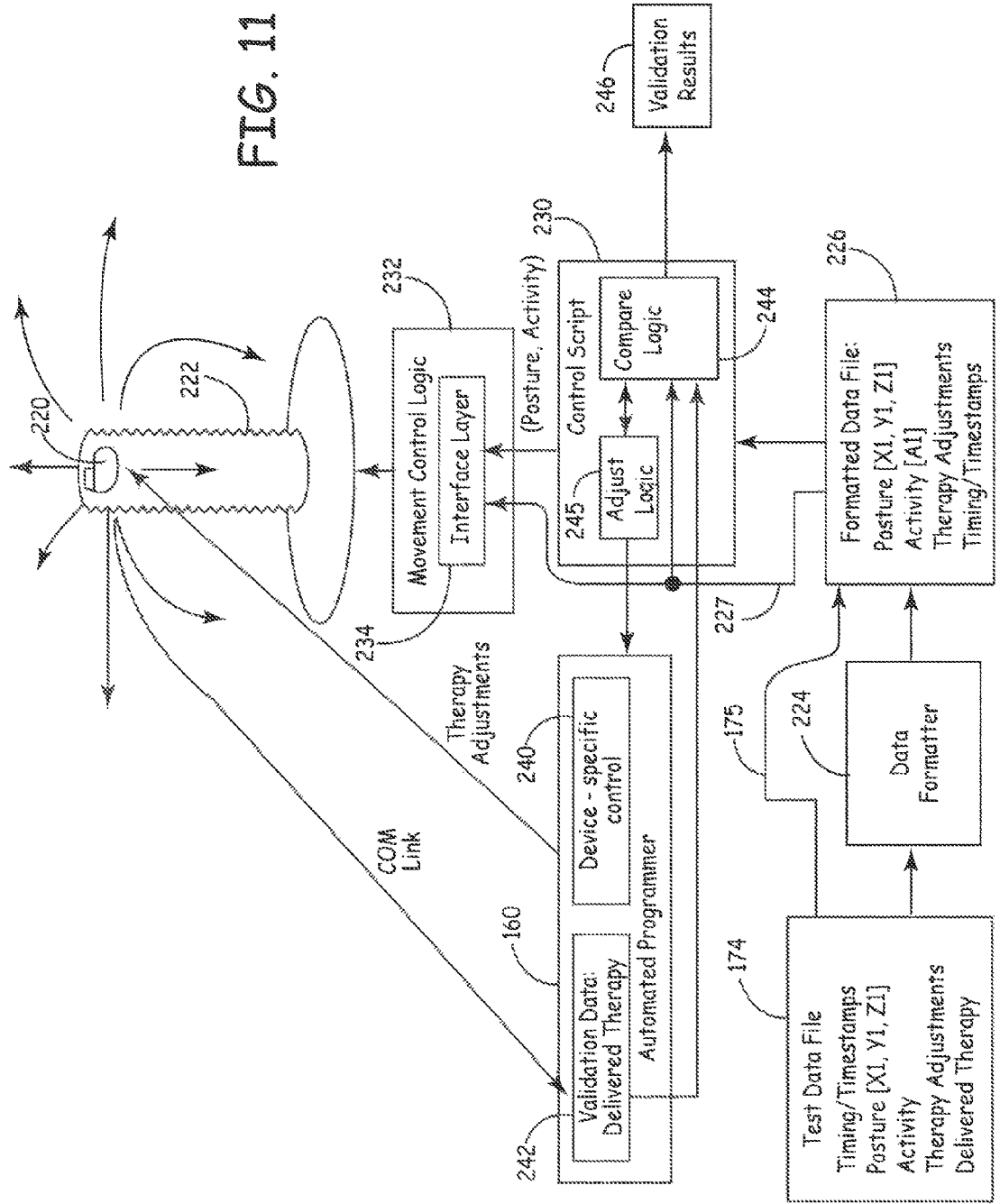
FIG. 11 is a block diagram of an automated system that utilizes data collected according to the techniques described herein to validate operation of an IMD.

FIG. 11 is a block diagram of an automated system that utilizes data collected according to the techniques described herein to validate operation of an IMD 220 during a validation phase. The IMD 220 has a similar therapy delivery module (e.g., therapy delivery module 32 of FIG. 2) to that of IMD 154 used during the data collection described above. In one embodiment, IMD 220 may have a measurement module 42 similar to that included in IMD 154. Finally, IMD 220 includes a sensor that may correspond to that of sensor logic 152. In the current embodiment, this sensor is capable of detecting posture states of a patient.

Unlike IMD 154 used during the data collection phase, IMD 220 is adapted to execute a closed-loop algorithm that utilizes data such as that shown in the table of FIG. 7 to control therapy delivery module 32. In one embodiment, the data contained within this table will be pre-loaded into IMD 154 before the validation phase commences. This data is derived from an analysis of the data in test data file 174. That is, each entry of the table will associate one or more patient parameter values (e.g., a posture vector and/or an activity level) obtained by sensor logic 152 during data collection with therapy parameter values indicative of a therapy adjustment made by a patient. This data may then be used by IMD 220 to control therapy delivery from the start of the validation phase, as will be described below.

It may be noted that some pre-processing of the data contained within test data file 174 will likely be necessary to create the table that will be pre-loaded on IMD 220. This is the result of several factors. First, during data collection, patient 150 may adjust therapy inconsistently in response to a certain set of patient parameter values. For instance, the patient 150 may only adjust therapy some of the time when transitioning from a sitting to a standing position. This may be the result of the burden placed on the patient to perform the therapy adjustments. As an example, the patient may not bother to adjust therapy if the patient knows the standing position will be assumed only temporarily. In addition, the patient's physical condition (e.g., pain state) may change from day-to-day. As a result, the patient may desire more or less stimulation when assuming a given posture state than was required the day before, for example. Thus, prior to pre-loading a table onto IMD 220, some processing of data in test data file 174 is needed to derive a one-to-one correspondence between patient parameter values and therapy parameter values.

As an example of the foregoing, pre-processing may first classify each set of patient parameters into one of multiple pre-defined posture states. Such classification could be performed in a manner described in U.S. patent application Ser. Nos. 12/433,004 and 12/432,993 referenced above. Other forms of classification are possible.

Once the patient parameter values are grouped into posture states, processing may utilize some mechanism (determining average or median values) to obtain a single set of therapy parameter values that correspond to the patient parameter values for the posture state. This will yield a single table entry that provides patient parameter values and associated therapy parameter values for a given posture. In this manner, pre-processing may be performed on data within test data file 174 to generate a table to be pre-loaded on IMD 220 for use in performing validation. Along with this table, IMD 220 will also be pre-loaded with control logic (e.g., software and/or firmware) to implement a closed-loop algorithm that will control therapy delivery module 32 to deliver therapy according to the data in the pre-loaded table.

After being configured in the above-described manner, IMD 220 may be affixed to an automated device 222 that is adapted to re-create the patient conditions that existed during data collection. In the current example, automated device 222 is a robotic arm that is capable of positioning IMD 220 to be in any orientation in three-dimensional space, and is further capable of re-creating any type of activity (e.g., activity levels) recorded by a three-axis accelerometer to indicate patient activity, as reflected by records 164, and optionally records 168. In one embodiment, robotic arm 222 is a model LR-200iC available from FANUC Robotics America, Inc., Rochester Hills, Mich., although other types of automated devices and robotics technologies may be employed.

IMD 220 must be affixed to automated device 222 via a test fixture. This test fixture is oriented in a known manner such that the sensor of IMD 220 is in a predetermined position relative to the automated device 222. In one embodiment, this predetermined position substantially aligns the axis of a three-axis accelerometer to three corresponding axes of movement of a robotic arm.

Test data file 174 is provided as input to the system of FIG. 11. As discussed above, test data includes the associations between patient parameter values recorded by sensor logic 152 in records 164, and therapy parameter values recorded by patient programmer 158 in records 162. This type of file may be generated by data analysis logic 172.

Test data of test data file 174 may be stored within a memory of automated programmer 160, a memory of a personal computer, within a memory of a server, a storage medium such as a DVD, CD, flash drive, and/or any other storage device. This data may be made accessible to the system of FIG. 11 using a hardwired or wireless communication link, via a network connection such as a secure intranet or an Internet connection that has the capability to access the data, by loading the test data 174 from a storage medium, etc.

Test data file 174 may be in any format generated by data analysis logic 172 (FIG. 8), or in the closed-loop embodiment, in a format generated by patient programmer 158. In one embodiment, the format provided by data analysis logic 172 is a Comma-Separated Values (CSV) format that may be provided as input directly to control movement of automated device 222. Thus, no data formatting is needed, and test data file 174 may be used as the formatted data file 226 that is provided as input to control automated device 222. This is as indicated by arrow 175. In an alternative embodiment wherein this is not the case, a data formatter 224 may be employed to manipulate the data included in test data file 174 so that it is in a format expected for use by automated device 222.

In the current embodiment, the formatted file 226 describes a sequence of posture states that each describes at least one of a posture (e.g., in the form of a vector) and an activity (e.g., an activity level). This sequence of posture states corresponds to the sequence of posture states that patient 150 assumed during data collection. Such a sequence may span the entire time period during which data collection occurred (e.g., three days, in one embodiment).

In one embodiment, the raw patient parameter data contained in formatted data file 226 is provided to interface layer 234 of movement control logic 232 of automated device 222. This is as indicated by arrow 227. In an alternative embodiment, the patient parameter data is delivered to interface layer 234 via a control script 230. In either case, delivery of this data is used by movement control logic 232 to cause automated device 222 to recreate the posture states that were experienced by patient 150 during data collection.

Movement control logic 232 includes the hardware, software, and/or firmware to control operation of automated device 222. In particular, the interface layer contains firmware and/or software routines to translate the patient parameter values (e.g., vectors and activity level parameters) from the formatted data file 226 into commands that control the hardware of automated device 222. In this manner, automated device 222 reproduces the orientations and movements represented by the patient parameter values. When IMD 220 is affixed to automated device 222 in a predetermined manner, IMD 220 will be subjected to the same sequence of orientations and movements as those to which IMD 154 was subjected during data collection. In a preferred embodiment, this occurs in real-time such that the time period during which re-enactment occurs corresponds to the time period used for data collection. The posture states of one embodiment each include at least one of a posture vector that controls orientation and an activity level that controls a level of movement.

As discussed above, IMD 220 must be affixed to automated device 222 in a predetermined manner to obtain accurate results. In one embodiment, this involves utilizing a test fixture that aligns an axis of an accelerometer included within the IMD with the axis of automated device 222. In this manner, when interface layer 234 responds to a vector [X1, Y1, and Z1] provided by test data file 174, the sensor (e.g., sensor 40) of IMD 220 will likewise generate a posture vector of [X1, Y1, and Z1]. Alternatively, this may be accomplished by calibrating sensor 40 of IMD 220 so that sensor 40 produces the desired vector reading when automated device 222 is responding to that vector in the test data. Such calibration of sensor 40 of IMD 220 may be performed programmably using a clinician programmer or automated programmer 160.

In addition to ensuring that IMD 220 is affixed and/or calibrated properly prior to commencing validation, some verification is also needed to ensure that interface layer 234 is accurately controlling automated device 222 to reproduce orientations and motions performed by patient 150 during data collection. For example, when a vector [X1, Y1, Z1] and an activity level of A1 is provided to interface layer 234, automated device 220 must respond by positioning IMD 220 in an orientation, and/or subjecting this device to a level of movement such that sensor 40 of IMD 220 also generates vector [X1, Y1, Z1] and/or an activity level of A1. A verification mechanism for ensuring that interface layer 234 is responding properly is described below in reference to FIG. 12. For purposes of this discussion, it will be assumed that verification of interface layer 234 has already been performed.

In the foregoing manner, IMD 220 is affixed to automated device 222, calibration is performed, and patient parameter values from formatted data file 226 are provided to interface layer 234. This causes automated device 222 to begin reproducing the posture states assumed by patient 150 during data collection, thereby subjecting IMD 220 to the same sequence of posture states as occurred during data collection.

As IMD 220 is subjected to various posture states, the sensor of IMD 220 senses the posture states and provides patient parameter values indicative of the posture states. Assuming IMD 220 has been pre-loaded with a table to enable closed-loop therapy adjustment in the foregoing manner, these patient parameter values are used by IMD 220 to reference the table and locate an associated set of therapy parameter values. These located therapy parameter values are provided to therapy delivery module 32 for use in controlling therapy delivered by IMD 220.

While this is occurring, measurement module 42 of IMD 220 is monitoring the therapy delivery module 32 to determine the therapy parameter values being used to deliver therapy. These therapy parameter values are communicated to automated programmer 160 as validation data 242, as may be accomplished via a wireless communication link (e.g., telemetry uplink session), or in another embodiment may be provided via a hardwired connection. This validation data 242, which includes the therapy parameter values, is forwarded to compare logic 244 of control script 230. Control script further has access to the therapy parameter values contained in formatted data file 226. Since re-enactment of the posture states is occurring in "real-time" (i.e., over a same time period as the posture states were assumed during data collection), control script 230 utilizes timestamps to locate the therapy parameter values from formatted data file 226 that correspond with the current validation time. The therapy parameter values from the formatted data file 226 should correspond closely with those included in the validation data 242.

In some cases, a miscompare between the therapy parameter values within formatted data file 226 and those contained within validation data 242 indicates a potential problem. For instance, hardware, software, and/or firmware of IMD 220 may not be detecting, and/or responding in an appropriate manner to, the posture states. If this is the case, an entry should be created in validation results 246 indicating that a potential problem exists. This entry may include data such as a timestamp indicating the time during validation when the miscompare occurred, the measured therapy parameter values from the IMD 220, and the therapy parameter values from formatted data file 226. Other data may include the patient parameter values used by automated device 222 to re-create the posture state, as well as patient parameter values sensed by IMD 220 at a time leading up to, or during, the miscompare. This information is then available to diagnose potential problems with the design of IMD 220.

In some circumstances, when a miscompare results, it is desirable to perform therapy adjustments. In these cases, control script 230 obtains the therapy parameter values available from the formatted data file 226, and provides these values to automated programmer 160 via either a hardwired or wireless communication link. Automated programmer 160 then communicates these values to IMD 220. This is generally accomplished via a wireless communication link (e.g., a telemetry downlink session) although a hardwired connection could be used in the alternative. Therapy delivery module 32 of IMD 220 should respond to these adjustments by changing therapy in accordance with the adjustments. This may be confirmed by measurement module 42, which determines the therapy parameter values being used to deliver the therapy, communicates these measurements as validation data 242 to automated programmer 160, which then forwards these values to control script 230 for validation. That is, compare logic 244 of control script 230 will again compare the therapy parameter values from the validation data 242 with those obtained from formatted data file 226 and communicated to IMD 220. This compare will validate that the adjustment was completed properly. If not, an entry may be created in validation results 246 in a manner similar to that described above.

In some cases, miscompare situations may be detected that are not related to a potential problem associated with IMD 220. As discussed above, during data collection, a patient may only adjust therapy some of the time when making a posture state transition. For instance, the patient may not bother to adjust therapy when the patient knows that a posture state will be assumed only briefly rather than being sustained for a longer period of time. Since during the validation phase, the IMD 220 uses a closed-loop algorithm and data in the pre-loaded table to automatically adjust therapy in response to all posture changes (including those for which the patient did not bother to perform adjustment), a miscompare may result in these situations. This is not the result of a potential problem, but rather indicates the IMD 220 is adjusting therapy consistently each time a given posture state is detected, whereas the patient adjustments may not have been as consistent. In these types of situations, it may not be desirable to create a log entry in validation results 246 to indicate a potential fault. Moreover, it may not be desirable to prompt IMD 220 to perform a therapy adjustment, since the therapy level is already appropriate based on the closed-loop algorithm and pre-loaded table data.

As another example, the patient's physical condition (e.g., pain state) may change from day-to-day. As a result, the patient may desire more or less stimulation when assuming a given posture state than was required the day before, for example. Recall that the therapy level in the pre-loaded table of the IMD will contain some base level therapy value that may have been derived by processing (e.g., averaging) all recorded patient adjustments received while the patient assumed a given posture state. Thus, the therapy as delivered by IMD 220 may not precisely match the therapy parameter values contained in the formatted data file 226 such that a miscompare results. In this case, it may not be desirable to create an entry in validation results 246, but it may nevertheless be desirable to provide the incremental therapy adjustment to IMD 220 via automated programmer 160, since this will most closely mimic how the IMD 220 will be operating in day-to-day use by a patient.

Several mechanisms may be used by control script 230 to detect and manage the foregoing types of situations. In one embodiment, the table that is pre-loaded onto IMD 220 for use in performing closed-loop therapy adjustment may be made accessible to control script 230. When a miscompare results, control script 230 may compare the therapy parameter values measured by measurement module 42 of IMD 220 to those contained in the applicable table entry that corresponds to the patient's posture state that was being assumed at the time the therapy parameter values were measured. If the measured therapy is consistent with these therapy parameter values, it is determined that the IMD is responding appropriately to the closed-loop mechanism in use at that time. In this case, it may be desirable to omit a step of creating an entry in validation results 246, since the miscompare is likely the result of inconsistent patient adjustments. Alternatively, an entry may be created in validation results 246 indicating that the delivered therapy was consistent with the table data but inconsistent with therapy parameter values obtained during data collection. On the other hand, if the measured therapy is not consistent with the parameters in the pre-loaded table, it may be desirable to create an entry in validation results 246 to indicate that a closer analysis of the situation by technicians is warranted.

In the foregoing cases, a determination must also be made as to whether to request an incremental therapy adjustment. Several embodiments exist. In one case, all such mis-compares could be handled by control script 230 issuing a therapy adjustment request to automated programmer 160 to adjust therapy according to the therapy parameter values of formatted data file 226. Alternatively, such adjustments may only be requested when the actual therapy delivered by IMD 220 is within some tolerance (e.g., some percentage value) of that reflected by the therapy parameter values of the formatted data file 226. This will generally result in therapy adjustments for those cases wherein the patient's selected therapy varies incrementally from day-to-day, for instance. However, this will likely not result in therapy adjustments for those scenarios wherein the patient neglected entirely to initiate adjustments such that the delivered therapy was significantly different from that recorded in formatted data file 226. This type of operation may be desired since it most closely mimics how IMD 220 will be used in real-life situations.

The types of determinations and decisional logic described above may be embodied by adjust logic 245 of control script 230. This logic may be provided to determine how to handle miscompares, including whether to create an entry in validation results 246 and/or whether to request an adjustment via automated programmer 160 in response to such a miscompare. Adjust logic 245 may be configured according to preferences of the technicians performing validation. In one embodiment, adjust logic 245 may be programmable, allowing the technicians to determine the types of situations in which entries are created in validation results 246 to report potential problems, and/or when to issue adjustments as a result of a miscompare.

The foregoing description discusses a situation wherein IMD 220 is pre-loaded with a table to control closed-loop operation of IMD 220. Thus, IMD 220 commences closed-loop operation at the start of the validation phase. In another embodiment, IMD 220 may build the table that will be used for closed-loop operation from the data contained in the formatted data file. In this embodiment, when the validation phase commences, control script 230 will provide the therapy parameter values from formatted data file 226 to automated programmer 160, which will, in turn, communicate these adjustments to IMD 220. IMD 220 will record the therapy parameter values in a table in association with the patient parameter values that were being sensed by the sensor of the IMD (e.g., sensor 40) contemporaneously with the receipt of the therapy parameter values. In addition, IMD 220 will adjust therapy accordingly.

Therapy adjustments made by IMD 220 will be detected by measurement module 42, communicated as validation data 242 to automated programmer 160, and forwarded to compare logic 244 for comparison against the therapy parameter values from formatted data file 226. A miscompare may result in the creation of an entry in validation results 246 in the manner described above.

In the above-described manner, at the outset of the validation phase, IMD 220 will receive therapy adjustments that are used to populate a table creating associations between patient parameter values and therapy parameter values. As this table is populated, a set of therapy parameter values will eventually be retrieved from formatted data file 226 by control script 230 that is associated with a posture state for which a table entry already exists. That is, IMD 220 has already handled this posture state at least once before during validation. It may be desirable for control script 230 to detect this type of scenario so it may be handled appropriately. One way control script 230 may detect this scenario is by using a same, or similar algorithm, as is being used by IMD 220 to build a table that duplicates that being built by IMD 220. This table may then be used by control script 230 to determine whether an entry already exists for a given posture state described by patient parameter values.

When control script 230 determines that therapy parameter values have been obtained from formatted data file 226 that are associated with patient parameter values that are already represented by a table entry, several courses of action may be taken. In one scenario, control script 230 may delay issuing a therapy adjustment to automated programmer 160. Instead, control script may wait until IMD 220 has an opportunity to adjust therapy according to the table values. Measurement module 42 of IMD 220 will convey detected therapy parameter values to automated programmer 160, which will forward these values to control script 230 for validation. If they correspond to the therapy parameter values of the applicable table entry, control script 230 can handle any mismatch between the measured values and the therapy parameter values in one of the ways described above. That is, if the measured values correspond to the table values, control script may forego creating an entry in validation results 246, and may additionally prompt automated programmer 160 to adjust therapy only if the measured values and the values from formatted data file 226 are within a certain tolerance of one another. Alternatively, control script 230 may handle this type of scenarios by always creating an entry in validation results 246 and/or always issuing a request to adjust therapy according to the data in formatted data file 226. As yet another alternative, adjustments may never be issued to IMD 220 in this type of situation. Again, these decisions are largely design choices, and may be programmable in one embodiment by adjusting control settings associated with adjust logic 245.

As noted above, accurate operation of the system of FIG. 11 depends on the ability of interface layer 234 to control automated device 222 so that a sensor 40 of IMD 220 will produce the same patient parameter values as were produced by a sensor of sensor logic 152 during data collection. To ensure that is true, validation of interface layer 232 must be performed.

Figure 12:
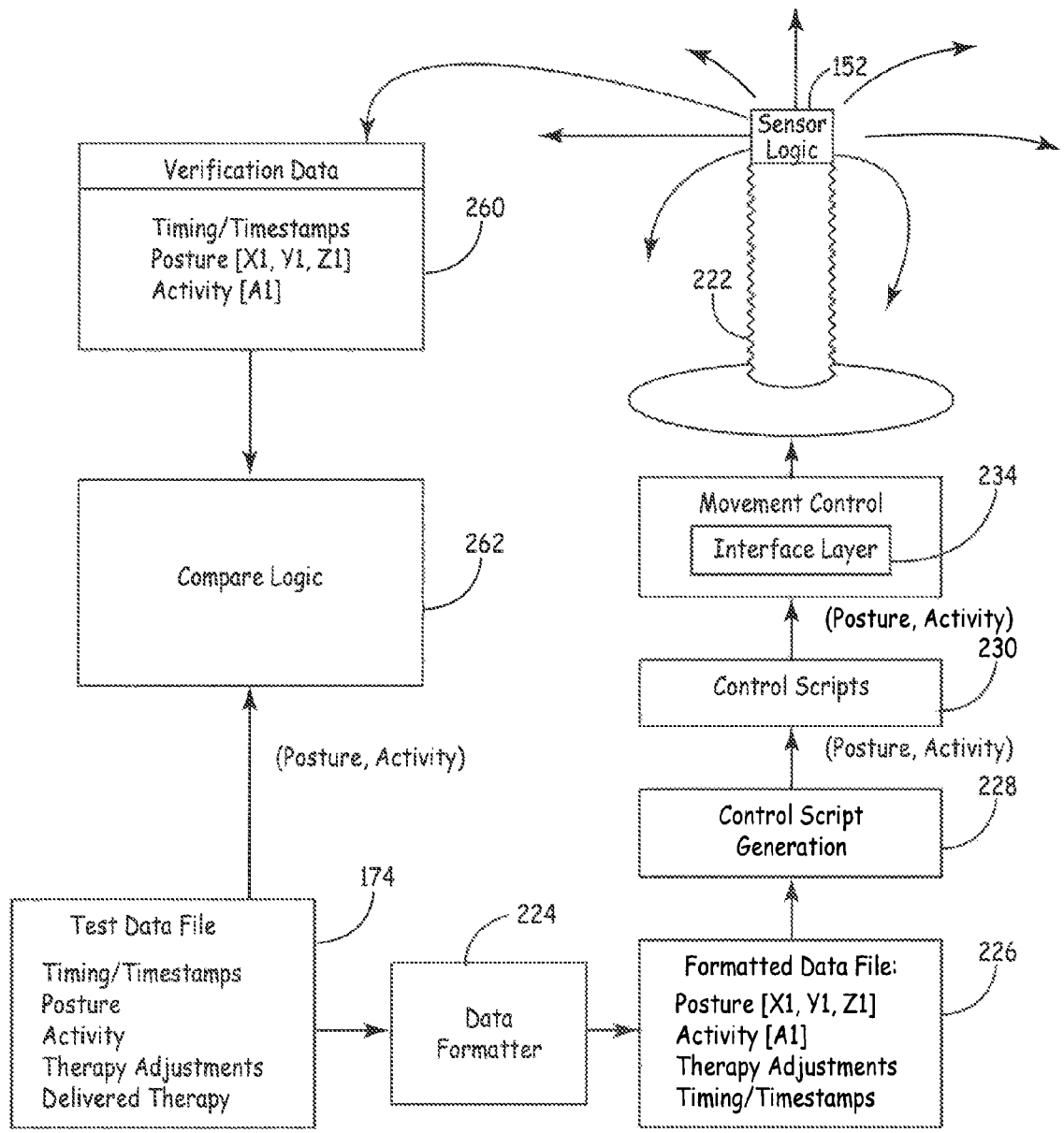
FIG. 12 is a block diagram of one system for validating control scripts.

FIG. 12 is a block diagram of one system for verifying that interface layer 234 of automated device 222 is operating to accurately reproduce the patient posture states. Many of the elements of FIG. 11 are included in the system of FIG. 12. A primary difference, however, is that in FIG. 12 sensor logic 152 is affixed to automated device 222 rather than IMD 220. Sensor logic 152, or logic similar to sensor logic 152, is coupled to automated device 222 and calibrated so that sensor 180 generates a predetermined calibration vector [X1, Y1, Z1] when the vector [X1, Y1, Z1] is interpreted by interface layer 234. Thereafter, the entire sequence of patient parameter values contained with test data file 174 is provided to interface layer 234. Assuming interface layer 234 accurately controls automated device 222 to re-create the posture states of patient that occurred during data collection, including both patient postures and activities, sensor logic 152 should generate the same output signals indicating the same posture states as those represented by test data file 174. To verify this, the output of sensor logic 152 is recorded as verification data 260. This recordation may be performed via a wireless or a hardwired communication link between sensor logic 152 and another device, such as automated programmer 160. The verification data is then compared by compare logic 262 to the posture and activity data included in test data 174. If the comparison indicates a difference between the two, interface layer 234 is not asserting proper control over automated device 222, or some other problem exists within the hardware of automated device itself. This situation must be addressed before validation of a device may be initiated.

Figure 13:
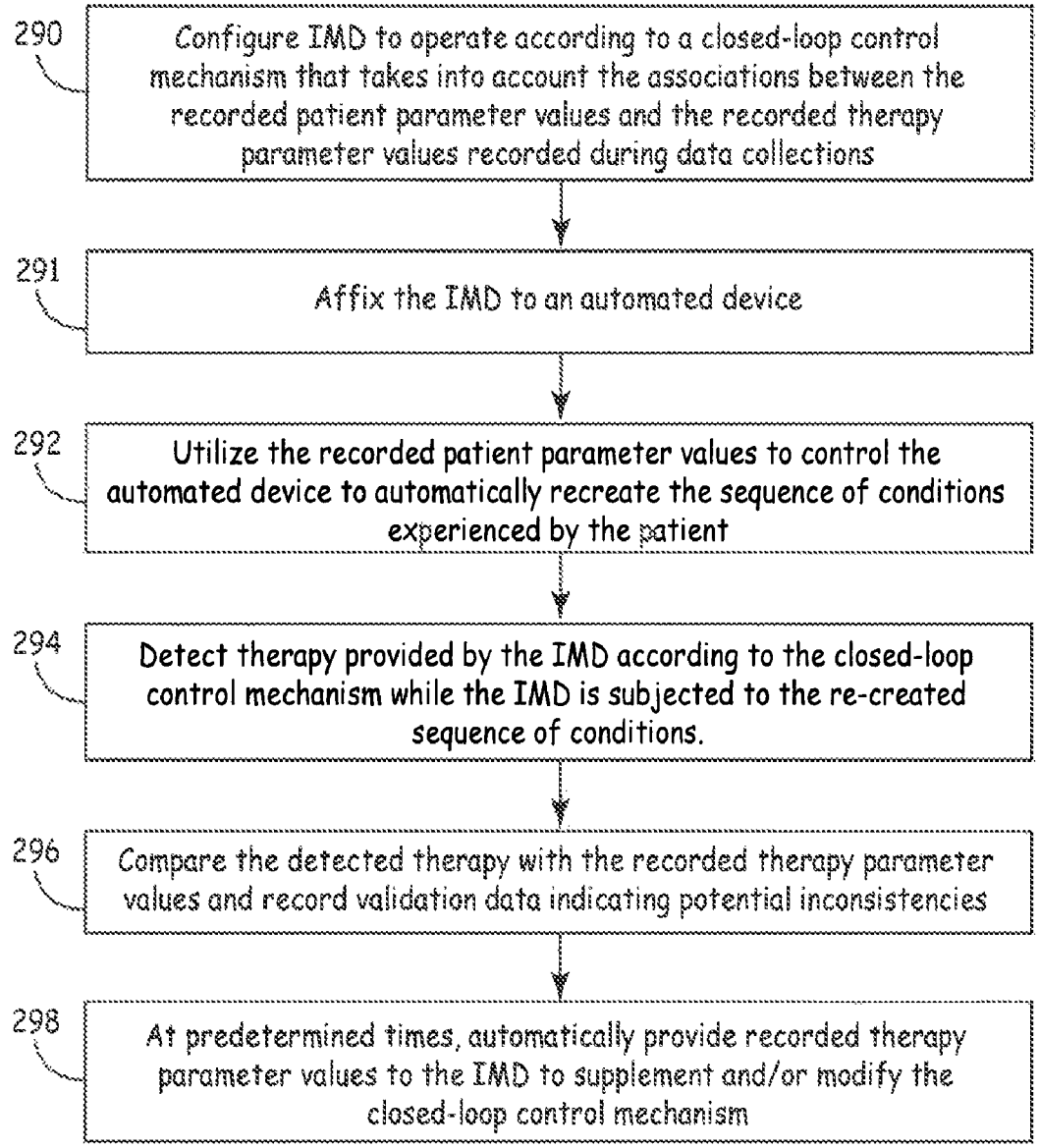
FIG. 13 is a flow diagram illustrating one method of performing data collection.

FIG. 13 is a flow diagram illustrating one method of performing validation of an IMD. The IMD is configured to operate according to a closed-loop control mechanism that takes into account the associations formed between the recorded patient parameter values and the therapy parameter values that were recorded during data collection (290). This IMD is affixed to an automated device (291), which may be a robotic arm. The recorded patient parameter values are utilized to control the automated device to automatically recreate the sequence of conditions experienced by the patient (292), which may be a sequence of posture states assumed by the patient during data collection. Therapy is provided by the IMD according to the closed-loop control mechanism while the IMD is subjected to the re-created sequence of conditions (294). Therapy provided by the IMD is detected and compared to the recorded therapy parameter values and validation data indicating potential inconsistencies between the two is recorded (296). At predetermined times, the recorded therapy parameter values obtained during data collection are provided to the IMD to supplement and/or modify the closed-loop control mechanism (298). This includes making adjustments to therapy when potential inconsistencies exist between detected therapy and the therapy that is expected. This also includes issuing therapy adjustments to the IMD at the start of the validation phase in an embodiment wherein the IMD is populating a data structure for controlling closed-loop operation at the start of the validation phase.

The foregoing examples describe automated techniques for testing a medical device which may, but need not, be an implantable device. The testing utilizes one or more sensors that detect posture states. Such sensors may include, but are not limited to, gyroscopes, accelerometers, strain gages, pressure transducers, impedance monitoring devices (e.g., for measuring thoracic impedance), electrodes to detect some other electrical signal produced by a living body, and so on. The one or more sensors may be appropriately positioned within the patient or on an external surface of the patient. It is understood that the described mechanisms are illustrative, and those skilled in the art may contemplate other embodiments and adaptations of these techniques. Therefore, the description above is not to be considered limiting, with the scope of the invention to be set forth by the claims that follow.

What is claimed is:

1. A method of testing a medical device, comprising:
   recording therapy parameter values describing therapy being delivered to a patient;
   recording a sequence of patient parameter values indicative of at least one of posture and activity of the patient occurring while the therapy is being delivered;
   controlling an automated device to reproduce the sequence of patient parameter values; and
   validating that the medical device is delivering therapy in accordance with the recorded therapy parameter values while the medical device is experiencing conditions resulting from controlling of the automated device.

2. The method of claim 1, further comprising utilizing an accelerometer to record the sequence of patient parameter values.

3. The method of claim 2, wherein recording the sequence of patient parameter values is performed by sensor logic carried by the patient.

4. The method of claim 1, wherein recording therapy parameter values is performed by a programmer.

5. The method of claim 4, wherein the programmer is receiving the patient parameter values from a sensor and is executing a closed-loop algorithm to control the therapy while the therapy parameter values are being recorded.

6. The method of claim 1, wherein the medical device is an implantable medical device for generating neurostimulation therapy.

7. The method of claim 1, further comprising:
   recording in an eDiary conditions indicative of the sequence of patient parameter values; and
   utilizing the recorded conditions to verify the sequence of patient parameter values.

8. The method of claim 1, wherein controlling the automated device to reproduce the sequence of patient parameter values comprises:
   attaching the medical device to the automated device;
   providing the recorded sequence of patient parameter values to control the automated device; and
   reproducing, by the automated device, conditions that resulted in sensing the sequence of patient parameter values.

9. The method of claim 8, wherein reproducing the conditions comprises orienting the medical device in one or more predetermined positions.

10. The method of claim 8, wherein reproducing the conditions comprises reproducing one or more predetermined activity states.

11. The method of claim 1, further comprising verifying that the sequence of patient parameter values is being reproduced accurately.

12. The method of claim 11, wherein verifying that the sequence of patient parameter values is being reproduced accurately comprises:
   utilizing an accelerometer to record a second sequence of patient parameter values during the reproducing step; and
   comparing the second sequence of patient parameter values to the sequence of patient parameter values.

13. The method of claim 1, wherein validating that the medical device is delivering therapy in accordance with the recorded therapy parameter values comprises comparing second therapy parameter values describing the therapy delivered by the medical device to the recorded therapy parameter values.

14. The method of claim 13, wherein validating that the medical device is delivering therapy in accordance with the recorded therapy parameters comprises delivering, by the medical device, therapy in response to a closed-loop algorithm.

15. The method of claim 14, wherein recording therapy parameter values comprises operating the medical device in response to an open-loop algorithm.

16. The method of claim 13, further comprising at least one of measuring by the medical device the therapy parameter values and measuring by the medical device the second therapy parameter values.

17. The method of claim 1, wherein the medical device comprises a sensor, and wherein validating that the medical device is delivering therapy in accordance with the recorded therapy parameter values comprises causing the sensor to substantially generate the sequence of patient parameter values.

18. The method of claim 17, further comprising delivering, by the medical device, therapy according to a closed-loop algorithm in response to the generated sequence of patient parameter values.

19. The method of claim 1, further comprising automatically providing therapy adjustments to the medical device that correspond to the recorded therapy parameter values while reproducing the sequence of patient parameter values.

20. The method of claim 1, wherein the medical device is an implantable medical device, and wherein recording therapy parameter values describing therapy being delivered to a patient comprises transferring the therapy parameter values to a storage device external to the patient.

21. A system for testing a medical device, comprising:
   means for recording therapy parameter values describing therapy being delivered to a patient;
   means for recording a sequence of patient parameter values indicative of at least one of posture and activity of the patient occurring while the therapy is being delivered;
   means for controlling an automated device to reproduce the sequence of patient parameter values; and
   means for validating that the medical device is delivering therapy in accordance with the recorded therapy parameter values while the medical device is experiencing conditions resulting from controlling of the automated device.

22. The system of claim 21, wherein the means for recording the sequence of patient parameter values comprises an accelerometer.

23. The system of claim 21, wherein the means for recording the sequence of patient parameter values comprises sensor logic carried by the patient.

24. The system of claim 21, wherein the means for recording therapy parameter values comprises a programmer.

25. The system of claim 24, wherein the programmer is configured to receive the patient parameter values from a sensor and to execute a closed-loop algorithm to control the therapy while the therapy parameter values are being recorded.

26. The system of claim 21, wherein the means for controlling an automated device comprises means for controlling the automated device to reproduce conditions that resulted in sensing the sequence of patient parameter values.

27. The system of claim 26, wherein the means for controlling an automated device comprises means for causing the automated device to orient the medical device in one or more predetermined positions.

28. The system of claim 21, further comprising means for verifying that the sequence of patient parameter values is being reproduced accurately.

29. A system for testing a medical device, comprising:
- a storage device configured to record therapy parameter values describing therapy being delivered to a patient;
- a storage device configured to record a sequence of patient parameter values indicative of at least one of posture and activity of the patient occurring while the therapy is being delivered;
- an automated device controlled to reproduce the sequence of patient parameter values; and
- logic configured to validate that the medical device is delivering therapy in accordance with the recorded therapy parameter values while the medical device is experiencing conditions resulting from controlling of the automated device.

30. The system of claim 29, further comprising sensor logic configured to detect the sequence of patient parameter values.

31. The system of claim 29, wherein the storage device that is configured to record therapy parameter values and the storage device that is configured to record the sequence of patient parameter values is a same storage device.

32. The system of claim 29, further comprising a processor configured to receive the patient parameter values from a sensor and to execute a closed-loop algorithm to control delivery of the therapy while the therapy parameter values are being recorded in the storage device.

33. The system of claim 32, further comprising a programmer comprising the processor.

34. The system of claim 29, wherein the logic configured to validate that the medical device is delivering therapy in accordance with the recorded therapy parameter values comprises logic configured to automatically orient the medical device in multiple positions.

35. The system of claim 29, wherein the logic configured to validate that the medical device is delivering therapy in accordance with the recorded therapy parameter values comprises logic configured to automatically orient the medical device to reproduce the sequence of patient parameter values.

* * * * *